US007354594B2

(12) United States Patent
Chen et al.

(10) Patent No.: US 7,354,594 B2
(45) Date of Patent: Apr. 8, 2008

(54) MEROZOITE SURFACE PROTEIN 1 LACKING GLYCOSYLATION SITES

(75) Inventors: Li How Chen, Acton, MA (US); Harry M. Meade, Newton, MA (US)

(73) Assignee: GTC Biotherapeutics, Inc., Framingham, MA (US)

( * ) Notice: Subject to any disclaimer, the term of this patent is extended or adjusted under 35 U.S.C. 154(b) by 199 days.

(21) Appl. No.: 11/140,676

(22) Filed: May 27, 2005

(65) Prior Publication Data

US 2005/0235371 A1 Oct. 20, 2005

Related U.S. Application Data

(60) Division of application No. 10/082,018, filed on Feb. 20, 2002, now abandoned, which is a continuation of application No. 09/175,684, filed on Oct. 20, 1998, now Pat. No. 6,593,463.

(60) Provisional application No. 60/085,649, filed on May 15, 1998, provisional application No. 60/062,592, filed on Oct. 20, 1997.

(51) Int. Cl.
*A61K 39/015* (2006.01)
*A61K 39/02* (2006.01)
*C12P 21/00* (2006.01)
*A01K 67/027* (2006.01)

(52) U.S. Cl. .............. 424/268.1; 424/191.1; 800/7; 800/14; 800/15; 800/16; 800/17; 800/18; 530/395; 514/12

(58) Field of Classification Search .......... 530/395; 424/191.1, 268.1; 800/7, 14–18; 514/12
See application file for complete search history.

(56) References Cited

U.S. PATENT DOCUMENTS

| | | |
|---|---|---|
| 4,873,316 A | 10/1989 | Meade et al. |
| 5,194,587 A | 3/1993 | Knapp et al. |
| 5,225,534 A | 7/1993 | Certa |
| 5,231,168 A | 7/1993 | Dziegiel et al. |
| 5,304,489 A | 4/1994 | Rosen |
| 5,395,614 A | 3/1995 | Knapp et al. |
| 5,530,177 A | 6/1996 | Bleck et al. |
| 5,543,323 A | 8/1996 | Ridley et al. |
| 5,643,578 A | 7/1997 | Robinson et al. |
| 5,646,247 A | 7/1997 | Barnwell et al. |
| 5,736,131 A | 4/1998 | Bosch et al. |
| 5,795,737 A | 8/1998 | Seed et al. |
| 5,856,178 A | 1/1999 | White et al. |
| 6,114,148 A | 9/2000 | Seed et al. |
| 6,130,062 A | 10/2000 | Milland et al. |
| 6,593,463 B1 | 7/2003 | Chen et al. |
| 2002/0144299 A1 | 10/2002 | Chen et al. |
| 2005/0071890 A1 | 3/2005 | Chen et al. |
| 2005/0235371 A1 | 10/2005 | Chen et al. |

FOREIGN PATENT DOCUMENTS

| | | |
|---|---|---|
| AU | 1997 48649 B2 | 4/1998 |
| AU | 727864 | 1/2001 |
| EP | 0264166 | 4/1988 |
| EP | 0359472 | 3/1990 |
| EP | 0682115 | 11/1995 |
| EP | 0923308 | 11/1997 |
| WO | WO-91/08216 | 6/1991 |
| WO | WO 91/18922 | 12/1991 |
| WO | WO 94/05796 | 3/1994 |
| WO | WO-94/28930 | 12/1994 |
| WO | WO 95/17085 | 6/1995 |
| WO | WO 96/03051 | 2/1996 |
| WO | WO 97/26911 | 7/1997 |
| WO | WO 97/30158 | 8/1997 |
| WO | WO 97/30159 | 8/1997 |
| WO | WO-97/31115 | 8/1997 |
| WO | WO-98/14583 | 4/1998 |
| WO | WO-99/20766 | 4/1999 |
| WO | WO-99/20774 | 4/1999 |

OTHER PUBLICATIONS

Holder et al. Primary Structure of the Precursor to the Three Major Surface Antigens of *Plamodium falciparum* Meroziotes. Nature. Sep. 19, 1985, vol. 317, pp. 270-273.*
Holder et al. Processing of the Precursor to the Major Meroziote Surface Antigens of *Plasmodium falciparum*. Parasitology. 1987, vol. 94, pp. 199-208.*
Siddiqui et al. Merozoite Surface Coat Precursor Protein Completely Protects Aotus Monkeys Against *Plasmodium falciparum* Malaria. Proced. Natal. Acad. Sci.. May 1987, vol. 84, pp. 3014-3018.*
[No Author Listed] Product pd(N)6 in the Pharmacia Biotech Catalogue. 1995. p. 277.
GenBank Submission; NIH/NCBI, Accession No. L48364. Lukashov et al. Feb. 28, 1996.
Akashi et al., Number and location of AUUUA motifs: role in regulating transiently expressed RNAs. Blood. Jun. 1, 1994;83(11):3182-7.
Brinster et al., Factors affecting the efficiency of introducing foreign DNA into mice by microinjecting eggs. Proc Natl Acad Sci U S A. Jul. 1985;82(13):4438-42.
Buhler et al., Rabbit beta-casein promoter directs secretion of human interleukin-2 into the milk of transgenic rabbits. Biotechnology (N Y). Feb. 1990;8(2):140-3.

(Continued)

*Primary Examiner*—Deborah Crouch
(74) *Attorney, Agent, or Firm*—Wolf, Greenfield & Sacks, P.C.

(57) ABSTRACT

The invention provides modified recombinant nucleic acid sequences (preferably DNA) and methods for increasing the mRNA levels and protein expression of malarial surface protein MSP-1 which is known to be difficult to express in cell culture systems, mammalian cell culture systems, or in transgenic animals. The preferred protein candidates for expression using the recombinant techniques of the invention are MSP-1 proteins expressed from DNA coding sequences comprising reduced overall AT content or AT rich regions and/or mRNA instability motifs and/or rare codons relative to the native MSP-1 gene.

27 Claims, 10 Drawing Sheets

OTHER PUBLICATIONS

Campbell et al., Sheep cloned by nuclear transfer from a cultured cell line. Nature. Mar. 7, 1996;380(6569):64-6.

Chang et al., Generalized immunological recognition of the major merozoite surface antigen (gp195) of *Plasmodium falciparum*. Proc Natl Acad Sci U S A. Aug. 1989;86(16):6343-7.

Chang et al., A carboxyl-terminal fragment of *Plasmodium falciparum* gp195 expressed by a recombinant baculovirus induces antibodies that completely inhibit parasite growth. J Immunol. Jul. 15, 1992;149(2):548-55.

Chang et al., A recombinant baculovirus 42-kilodalton C-terminal fragment of *Plasmodium falciparum* merozoite surface protein 1 protects Aotus monkeys against malaria. Infect Immun. Jan. 1996;64(1):253-61.

Chattergoon et al., Genetic immunization: a new era in vaccines and immune therapeutics. FASEB J. Aug. 1997;11(10):753-63.

Dame et al., Current status of the *Plasmodium falciparum* genome project. Mol Biochem Parasitol. Jul. 1996;79(1):1-12.

Diggs et al., The major merozoite surface protein as a malaria vaccine target. Parasitol Today. Aug. 1993;9(8):300-2.

D'Orso et al., TcUBP-1, a developmentally regulated U-rich RNA-binding protein involved in selective mRNA destabilization in trypanosomes. J Biol Chem. Sep. 14, 2001;276(37):34801-9. Epub Jul. 2, 2001.

Ebert et al., Transgenic production of a varient of human tissue-type plasminogen activator in goat milk: generation of transgenic goats and analysis of expression. Biotechnology (N Y). Sep. 1991;9(9):835-8.

Gardner et al., DNA vaccines against malaria: immunogenicity and protection in a rodent model. J Pharm Sci. Dec. 1996;85(12):1294-300.

Gordon et al., Genetic transformation of mouse embryos by microinjection of purified DNA. Proc Natl Acad Sci U S A. Dec. 1980;77(12):7380-4.

Gordon et al., Integration and stable germ line transmission of genes injected into mouse pronuclei. Science. Dec. 11, 1981;214(4526):1244-6.

Graves et al., Comparison of the cost-effectiveness of vaccines and insecticide impregnation of mosquito nets for the prevention of malaria. Ann Trop Med Parasitol. Jun. 1998;92(4):399-410.

Graves et al., Vaccines for preventing malaria. Cochrane Database Syst Rev. 2003;(1):CD000129.

Gutierrez et al., Expression of a bovine kappa-CN cDNA in the mammary gland of transgenic mice utilizing a genomic milk protein gene as an expression cassette. Transgenic Res. Jul. 1996;5(4):271-9.

Hochi et al., Secretion of bovine alpha-lactalbumin into the milk of transgenic rats. Mol Reprod Dev. Oct. 1992;33(2):160-4.

Holder et al., Primary structure of the precursor to the three major surface antigens of *Plasmodium falciparum* merozoites. Nature. Sep. 19-25, 1985;317(6034):270-3.

Jenkins et al., Evolution of base composition and codon usage bias in the genus Flavivirus. J Mol Evol. Apr. 2001;52(4):383-90.

Jongwutiwes et al., Sequence conservation in the C-terminal part of the precursor to the major merozoite surface proteins (MSP1) of *Plasmodium falciparum* from field isolates. Mol Biochem Parasitol. May 1993;59(1):95-100.

Kalinna et al., DNA vaccines for parasitic infections. Immunol Cell Biol. Aug. 1997;75(4):370-5.

Krimpenfort et al., Generation of transgenic dairy cattle using 'in vitro' embryo production. Biotechnology (N Y). Sep. 1991;9(9):844-7.

Ledley et al., Clinical considerations in the design of protocols for somatic gene therapy. Hum Gene Ther. 1991 Spring;2(1):77-83.

Liebhaber et al., mRNA stability and the control of gene expression. Nucleic Acids Symp Ser. 1997;(36):29-32.

Martin et al., Total synthesis and expression in *Escherichia coli* of a gene encoding human tropoelastin. Gene. Mar. 10, 1995; 154(2):159-66.

McDonnell et al., DNA vaccines. N Engl J Med. Jan. 4, 1996;334(1):42-5.

Nuijens et al., Characterization of recombinant human lactoferrin secreted in milk of transgenic mice. J Biol Chem. Mar. 28, 1997;272(13):8802-7.

Orkin et al., Report and recommendations of panel to access NIH investment in Gene Therapy Res. 1995.

Palmiter et al., Transgenic mice. Cell. Jun. 1985;41(2):343-5.

Perlak et al., Modification of the coding sequence enhances plant expression of insect control protein genes. Proc Natl Acad Sci U S A. Apr. 15, 1991;88(8):3324-8.

Prapunwattana et al., Chemical synthesis of the *Plasmodium falciparum* dihydrofolate reductase-thymidylate synthase gene. Mol Biochem Parasitol. Dec. 2, 1996;83(1):93-106.

Senior et al., DNA vaccine shows promise for malaria. Mol Med Today. Jan. 1999; 5(1):2-3.

Shani et al., Expression of human serum albumin in the milk of transgenic mice. Transgenic Res. Sep. 1992;1(5):195-208.

Shaw et al., A conserved AU sequence from the 3' untranslated region of GM-CSF mRNA mediates selective mRNA degradation. Cell. Aug. 29, 1986;46(5):659-67.

Simons et al., Gene transfer into sheep. Bio/Technology. 1988;6:179-83.

Soulier et al., Expression analysis of ruminant alpha-lactalbumin in transgenic mice: developmental regulation and general location of important cis-regulatory elements. FEBS Lett. Feb. 3, 1992;297(1-2):13-8.

Urdea et al., Chemical synthesis of a gene for human epidermal growth factor urogastrone and it expression in yeast. Proc Natl Acad Sci U S A. Dec. 1983;80(24):7461-5.

Velander et al., High-level expression of a heterologous protein in the milk of transgenic swine using the cDNA encoding human protein C. Proc Natl Acad Sci U S A. Dec. 15, 1992;89(24):12003-7.

Vilotte et al., Efficient tissue-specific expression of bovine alpha-lactalbumin in transgenic mice. Eur J Biochem. Dec. 8, 1989;186(1-2):43-8.

Wall et al., Development of porcine ova that were centrifuged to permit visualization of pronuclei and nuclei. Biol Repord. Apr. 1985;32(3):645-51.

Wall et al., Making transgenic livestock: genetic engineering on a large scale. J Cell Biochem. Jun. 1992;49(2):113-20.

Wang et al., Recombinant bovine alpha-lactalbumin obtained by limited proteolysis of a fusion protein expressed at high levels in *Escherichia coli*. J Biol Chem. Dec. 15, 1989;264(35):21116-21.

Weber et al., Analysis of sequences from the extremely A + T-rich genome of *Plasmodium falciparum*. Gene. 1987;52(1):103-9.

Wesseling et al., Nucleotide sequence and deduced amino acid sequence of a *Plasmodium falciparum* actin gene. Mol Biochem Parasitol. Jan. 15, 1988;27(2-3):313-20.

Wright et al., High level expression of active human alpha-1-antitrypsin in the milk of transgenic sheep. Biotechnology (N Y). Sep. 1991;9(9):830-4.

Wu et al., Transfection of *Plasmodium falciparum* within human red blood cells. Proc Natl Acad Sci U S A. Feb. 14, 1995;92(4):973-7.

Zientz et al., Genome interdependence in insect-bacterium symbioses. Genome Biol. 2001;2(12):REVIEWS1032. Epub Nov. 22, 2001.

Zinkernagel et al., Immunity to viruses. Chapter 34: Fundamental Immunology. 3rd Edition, Raven Press. 1993.

Carver et al., Expression of Human Alpha 1 Antitrypsin In Transgenic Sheep. Cytotechnology. 1992;9(1-3):77-84.

Eskridge et al.,The NH2 terminus of preproinsulin directs the translocation and glycosylation of a bacterial cytoplasmic protein by mammalian microsomal membranes. J. Cell. Biol. 103(6):2263-2272 (1996).

Hirabayashi et al., Transgene Expression In Mammary Glands of Newborn Rats. Mol. Reprod. Dev. Feb. 1996;43(2):145-9.

Holder et al., The precursor to major merozoite surface antigens: structure and role in immunity. Prog. Allergy. 41:72-97 (1988).

Kotula et al., Evaluation of foreign gene codon optimization in yeast: expression of a mouse IG kappa chain. Biotechnology 9(10):1386-1389.

Marshall et al., Naturally occurring splicing varients of the *hMSH2* gene containing nonsense codons identify possible mRNA instability motifs within the gene coding region, Biochimica et Biophysica Acta, Jul. 31, 1996; 1308(1):88-92.

Peterson et al., Variation in the precursor to the major merozoite surface antigens of *Plasmodium falciparum*. Mol. Biochem. Parisitol 27:291-302 (1988).

Prunkard et al., High-Level Expression o f Recombinant Human Fibrinogen In the Milk of Transgenic Mice. Nat. Biotechnol. Jul. 1996;14(7):867-71.

Reeck et al., Homology in proteins in nucleic acids: a terminology muddle and a way out of it. Cell Aug. 28, 1987; 50:667.

Van Cott et al., Affinity Purification of Biologically Active and Inactive Forms of Recombinant Human Protein C Produced In Porcine Mammary Gland. J. Mol. Recognit. Sep.-Dec. 1996; 9(5-6):407-14.

Wang et al., Molecular cloning, gene organization and expression of rainbow trout (*Oncorhynchus mykiss*) inducible nitric oxide synthase (iNOS) gene. J. Biochem. 2001; 358:747-55.

Ziomek Minimization of Viral Contamination In Human Pharmaceuticals Produced in the Milk of Transgenic Goats. Dev. Biol. Stand. 1996;88:265-8.

Myler, Nucleotide and deduced amino acids sequence of the gp195 (MSA-1) gene from Plasmodium falciparum Palo Alto PLF-3/B11. 1989 Nucleic Acids Research 17: 5401.

Romanos et al., Expression of tetanus toxin fragment C in yeast: gene synthesis is required to eliminate fortuitous polyadenylation in AT-rich DNA. 1991 Nucleic Acids Research 19: 1461-1467.

Notice of Allowance and Fees Due mailed Dec. 19, 2007 for U.S. Appl. No. 10/082,018 (G0744.70331US03, Chen et al., filed Feb. 20, 2002).

* cited by examiner

```
  1 GCCGTCACTCCCTCCGTCATCGATAACATCCTGTCCAAGATCGAGAAGGAGTACG
  1▶ Ala Val Thr Pro Ser Val Ile Asp Asn Ile Leu Ser Lys Ile Glu Asn Glu Tyr G
 56 AGGTGCTGTACCTGAAGCCGCTGGCAGGGGTCTACCGGAGCCTGAAGAAGCAG
 19▶ lu Val Leu Tyr Leu Lys Pro Leu Ala Gly Val Tyr Arg Ser Leu Lys Lys Gln
109 CTGGAGAACAACGTGATGACCTTCAACGTGAACGTGAAGGATATCCTGAACAGC
 37▶ Leu Glu Asn Asn Val Met Thr Phe Asn Val Asn Val Lys Asp Ile Leu Asn Ser
163 CGGTTCAACAAGCGGGAGAACTTCAAGAACGTGCTGGAGAGCGATCTGATCCC
 55▶ Arg Phe Asn Lys Arg Glu Asn Phe Lys Asn Val Leu Glu Ser Asp Leu Ile Pr
216 CTACAAGGATCTGACCAGCAGCAACTACGTGGTCAAGGATCCCTACAAGTTCC
 72▶ o Tyr Lys Asp Leu Thr Ser Ser Asn Tyr Val Val Lys Asp Pro Tyr Lys Phe L
269 TGAACAAGGAGAAGAGAGATAAGTTCCTGAGCAGTTACAACTACATCAAGGATAG
 90▶ eu Asn Lys Glu Lys Arg Asp Lys Phe Leu Ser Ser Tyr Asn Tyr Ile Lys Asp Se
324 CATTGATACCGATATCAACTTCGCCAACGATGTCCTGGGATACTACAAGATCCT
108▶ r Ile Asp Thr Asp Ile Asn Phe Ala Asn Asp Val Leu Gly Tyr Tyr Lys Ile Le
378 GTCCGAGAAGTACAAGAGCGATCTGGATTCAATCAAGAAGTACATCAACGATAA
126▶ u Ser Glu Lys Tyr Lys Ser Asp Leu Asp Ser Ile Lys Lys Tyr Ile Asn Asp Ly
432 GCAGGGAGAGAACGAGAAGTACCTGCCCTTCCTGAACAACATCGAGACCCTGTA
144▶ s Gln Gly Glu Asn Glu Lys Tyr Leu Pro Phe Leu Asn Asn Ile Glu Thr Leu Ty
486 CAAGACCGTCAACGATAAGATTGATCTGTTCGTGATCCACCTGGAGGCCAAGGT
162▶ r Lys Thr Val Asn Asp Lys Ile Asp Leu Phe Val Ile His Leu Glu Ala Lys Va
                                                          NdeI
540 CCTGAACTACACATATGAGAAGAGCAACGTGGAGGTCAAGATCAAGGAGCTGAA
180▶ l Leu Asn Tyr Thr Tyr Glu Lys Ser Asn Val Glu Val Lys Ile Lys Glu Leu As
594 TTACCTGAAGACCATCCAGGATAAGCTGGCCGATTTCAAGAAGAACAACTT
198▶ n Tyr Leu Lys Thr Ile Gln Asp Lys Leu Ala Asp Phe Lys Lys Asn Asn Ph
648 CGTCGGGATCGCCGATCTGAGCACCGATTACAACCAACAACCTGCTGACCAA
216▶ e Val Gly Ile Ala Asp Leu Ser Thr Asp Tyr Asn His Asn Asn Leu Leu Thr Ly
702 GTTCCTGAGCACCGGTATGGTCTTCGAAAACCTGGCCAAGACCGTCCTGAGCAA
234▶ s Phe Leu Ser Thr Gly Met Val Phe Glu Asn Leu Ala Lys Thr Val Leu Ser As
756 CCTGCTGGATGGGAACCTGCAGGGGATGCTGAACATCAGCCAGCACCAGTGTGT
252▶ n Leu Leu Asp Gly Asn Leu Gln Gly Met Leu Asn Ile Ser Gln His Gln Cys Va
810 GAAGAAGCAGTGTCCCCAGAACAGCGGGTGTTTCAGACACCTGGATGAGAGA
270▶ l Lys Lys Gln Cys Pro Gln Asn Ser Gly Cys Phe Arg His Leu Asp Glu Arg Gl
864 GGAGTGTAAGTGTCTGCTGAACTACAAGCAGGAAGGTGATAAGTGTGTGGAAAAC
288▶ u Glu Cys Lys Cys Leu Leu Asn Tyr Lys Gln Glu Gly Asp Lys Cys Val Glu Asn
919 CCAATCCTACTTGTAACGAGAACAATGGTGGATGTGATGCCGATGCCAAGTGTACCG
307▶ Pro Asn Pro Thr Cys Asn Glu Asn Asn Gly Gly Cys Asp Ala Asp Ala Lys Cys Thr G
977 AGGAGGATTCAGGGAGCAACGGAAGAAGATCACCTGTGAGTGTACCAAGCCTGATT
326▶ lu Asp Ser Gly Ser Asn Gly Lys Lys Ile Thr Cys Glu Cys Thr Lys Pro Asp S
1034 CTTATCCACTGTTCGATGGTATCTTCTGTAGT
345▶ er Tyr Pro Leu Phe Asp Gly Ile Phe Cys Ser
```

FIG. 1

1    GCAGTAACTCCTTCCGTAATTGATAACATACTTTCTAAAATTGAAAATGAATA
1▶  A l aVa l Thr ProSer Va l I l eAspAsn I l eLeuSer Lys I l eGl uAsnGl uTyrG
                                EcoNI (73)
56   AGGTTTTATATTTAAAACCTTTAGCAGGTGTTTATAGAAGTTTAAAAAAACAATT
19▶  l uVa l LeuTyrLeuLysProLeuA l aGl yVa l TyrArgSer LeuLysLysGl nLe
111  AGAAAATAACGTTATGACATTTAATGTTAATGTTAAGGATATTTTAAATTCACGA
37▶  uGl uAsnAsnVa l MetThr PheAsnVa l AsnVa l LysAsp I l eLeuAsnSer Arg
166  TTTAATAAACGTGAAAATTTCAAAAATGTTTAGAATCAGATTTAATTCCATATA
56▶  PheAsnLysArgGl uAsnPheLysAsnVa l LeuGl uSer AspLeu I l eProTyrL
221  AAGATTTAACATCAAGTAATTATGTTGTCAAAGATCCATATAAATTTCTTAATAA
74▶  ysAspLeuThr Ser Ser AsnTyrVa l Va l LysAspProTyrLysPheLeuAsnLy
276  AGAAAAAAGAGATAAATTCTTAAGCAGTTATAATTATATTAAGGATTCAATAGAT
92▶  sGl uLysArgAspLysPheLeuSer Ser TyrAsnTyr I l eLysAspSer I l eAsp
331  ACGGATATAAATTTTGCAAATGATGTTCTTGGATATTATAAAATATTATCCGAAA
111▶ ThrAsp I l eAsnPheA l aAsnAspVa l LeuGl yTyrTyrLys I l eLeuSer Gl uL
386  AATATAAATCAGATTTAGATTCAATTAAAAAATATATCAACGACAAACAAGGTGA
129▶ ysTyrLysSer AspLeuAspSer I l eLysLysTyr I l eAsnAspLysGl nGl yGl
441  AAATGAGAAATACCTTCCCTTTTTAAACAATATTGAGACCTTATATAAAACAGTT
147▶ uAsnGl uLysTyrLeuProPheLeuAsnAsn I l eGl uThr LeuTyrLysThr Va l
496  AATGATAAAATTGATTTATTTGTAATTCATTTAGAAGCAAAAGTTCTAAATTATA
166▶ AsnAspLys I l eAspLeuPheVa l I l eHi sLeuGl uA l aLysVa l LeuAsnTyrT
551  CATATGAGAAATCAAACGTAGAAGTTAAAATAAAAGAACTTAATTACTTAAAAAC
184▶ hr TyrGl uLysSer AsnVa l Gl uVa l Lys I l eLysGl uLeuAsnTyrLeuLysTh
606  AATTCAAGACAAATTGGCAGATTTTAAAAAAAATAACAATTTCGTTGGAATTGCT
202▶ r I l eGl nAspLysLeuA l aAspPheLysLysAsnAsnAsnPheVa l Gl y I l eA l a
661  GATTTATCAACAGATTATAACCATAATAACTTATTGACAAAGTTCCTTAGTACAG
221▶ AspLeuSer ThrAspTyrAsnHi sAsnAsnLeuLeuThr LysPheLeuSer Thr G
716  GTATGGTTTTTGAAAATCTTGCTAAAACCGTTTTATCTAATTTACTTGATGGAAA
239▶ l yMetVa l PheGl uAsnLeuA l aLysThr Va l LeuSer AsnLeuLeuAspGl yAs
771  CTTGCAAGGTATGTTAAACATTTCACAACACCAATGCGTAAAAAAACAATGTCCA
257▶ nLeuGl nGl yMetLeuAsn I l eSer Gl nHi sGl nCysVa l LysLysGl nCysPro
826  CAAAATTCTGGATGTTTCAGACATTTAGATGAAAGAGAAGAATGTAAATGTTTAT
276▶ Gl nAsnSer Gl yCysPheArgHi sLeuAspGl uArgGl uGl uCysLysCysLeuL
881  TAAATTACAAACAAGAAGGTGATAAATGTGTTGAAAATCCAAATCCTACTTGTAA
294▶ euAsnTyrLysGl nGl uGl yAspLysCysVa l Gl uAsnProAsnProThr CysAs
936  CGAAAATAATGGTGGATGTGATGCAGATGCCAAATGTACCGAAGAAGATTCAGGT
312▶ nGl uAsnAsnGl yGl yCysAspA l aAspA l aLysCysThr Gl uGl uAspSer Gl y
991  AGCAACGGAAAGAAAATCACATGTGAATGTACTAAACCTGATTCTTATCCACTTT
331▶ Ser AsnGl yLysLys I l eThr CysGl uCysThr LysProAspSer TyrProLeuP
                                Pst I (1059)
1046 TCGATGGTATTTTCTGCAGTCACCACCACCACCACCACTAACT
349▶ heAspGl y I l ePheCysSer Hi sHi sHi sHi sHi sHi s • • •

FIG. 2

| Codon | AA | goat b-casein | goat K-casein | MSP wt | Edited MSP | mouse b-casein | mouse a-casein | mouse g-casein | mouse e-casein |
|---|---|---|---|---|---|---|---|---|---|
| TTT | Phe | 5 | 4 | 8 | 0 | 4 | 8 | 3 | 4 |
| TTC | Phe | 4 | 3 | 7 | 15 | 4 | 6 | 7 | 1 |
| TTA | Leu | 0 | 2 | 25 | 0 | 0 | 0 | 0 | 0 |
| TTG | Leu | 0 | 2 | 3 | 0 | 0 | 0 | 0 | 1 |
| TCT | Ser | 5 | 1 | 4 | 1 | 13 | 5 | 7 | 5 |
| TCC | Ser | 2 | 2 | 2 | 3 | 6 | 14 | 8 | 2 |
| TCA | Ser | 1 | 4 | 10 | 1 | 1 | 3 | 2 | 0 |
| TCG | Ser | 0 | 1 | 0 | 0 | 0 | 0 | 0 | 0 |
| TAT | Tyr | 2 | 7 | 17 | 2 | 1 | 3 | 2 | 1 |
| TAC | Tyr | 1 | 2 | 3 | 18 | 2 | 6 | 6 | 7 |
| TAA | ... | 1 | 2 | 0 | 0 | 1 | 0 | 1 | 0 |
| TAG | ... | 0 | 0 | 0 | 0 | 0 | 0 | 0 | 0 |
| TGT | Cys | 1 | 1 | 10 | 12 | 0 | 0 | 1 | 0 |
| TGC | Cys | 0 | 2 | 2 | 0 | 2 | 2 | 2 | 1 |
| TGA | ... | 0 | 0 | 0 | 0 | 0 | 1 | 0 | 1 |
| TGG | Trp | 1 | 1 | 0 | 0 | 0 | 2 | 2 | 2 |
| CTT | Leu | 9 | 1 | 9 | 0 | 16 | 9 | 3 | 3 |
| CTC | Leu | 5 | 2 | 0 | 0 | 7 | 8 | 0 | 1 |
| CTA | Leu | 1 | 2 | 1 | 0 | 1 | 2 | 1 | 0 |
| CTG | Leu | 11 | 5 | 0 | 38 | 10 | 17 | 4 | 1 |
| CCT | Pro | 17 | 6 | 4 | 2 | 8 | 6 | 3 | 0 |
| CCC | Pro | 12 | 0 | 1 | 6 | 8 | 6 | 6 | 4 |
| CCA | Pro | 3 | 13 | 5 | 1 | 5 | 6 | 2 | 2 |
| CCG | Pro | 1 | 1 | 0 | 1 | 0 | 0 | 0 | 1 |
| CAT | His | 0 | 1 | 3 | 0 | 2 | 6 | 2 | 1 |
| CAC | His | 5 | 3 | 1 | 4 | 4 | 0 | 3 | 0 |
| CAA | Gln | 5 | 9 | 9 | 0 | 9 | 21 | 9 | 7 |
| CAG | Gln | 16 | 6 | 0 | 9 | 21 | 32 | 12 | 8 |
| CGT | Arg | 0 | 1 | 1 | 0 | 0 | 0 | 0 | 0 |
| CGC | Arg | 0 | 0 | 0 | 0 | 1 | 0 | 0 | 0 |
| CGA | Arg | 0 | 0 | 1 | 0 | 0 | 0 | 0 | 1 |
| CGG | Arg | 1 | 0 | 0 | 3 | 0 | 0 | 0 | 0 |
| ATT | Ile | 4 | 5 | 13 | 0 | 3 | 4 | 3 | 4 |
| ATC | Ile | 6 | 3 | 2 | 20 | 7 | 5 | 8 | 5 |
| ATA | Ile | 1 | 3 | 5 | 0 | 1 | 0 | 2 | 0 |
| ATG | Met | 7 | 3 | 3 | 3 | 4 | 12 | 2 | 13 |
| ACT | Thr | 7 | 6 | 3 | 2 | 6 | 5 | 1 | 4 |
| ACC | Thr | 2 | 7 | 3 | 13 | 4 | 4 | 4 | 4 |
| ACA | Thr | 2 | 4 | 9 | 1 | 1 | 1 | 2 | 0 |
| ACG | Thr | 0 | 0 | 1 | 0 | 0 | 0 | 2 | 0 |
| AAT | Asn | 2 | 6 | 29 | 3 | 4 | 6 | 3 | 1 |
| AAC | Asn | 2 | 3 | 12 | 38 | 4 | 9 | 4 | 6 |
| AAA | Lys | 7 | 6 | 38 | 0 | 6 | 7 | 3 | 5 |
| AAG | Lys | 6 | 4 | 4 | 42 | 3 | 6 | 13 | 7 |
| AGT | Ser | 2 | 6 | 5 | 2 | 3 | 6 | 6 | 5 |
| AGC | Ser | 5 | 0 | 2 | 16 | 2 | 6 | 6 | 3 |
| AGA | Arg | 2 | 2 | 4 | 3 | 1 | 8 | 1 | 1 |
| AGG | Arg | 0 | 2 | 0 | 0 | 0 | 0 | 0 | 1 |
| GTT | Val | 5 | 6 | 15 | 0 | 7 | 4 | 2 | 3 |
| GTC | Val | 8 | 2 | 1 | 11 | 7 | 3 | 3 | 0 |
| GTA | Val | 2 | 2 | 5 | 0 | 2 | 4 | 1 | 3 |
| GTG | Val | 8 | 4 | 0 | 10 | 6 | 3 | 5 | 3 |
| GCT | Ala | 1 | 3 | 2 | 0 | 8 | 17 | 4 | 2 |
| GCC | Ala | 4 | 7 | 1 | 8 | 6 | 3 | 3 | 3 |
| GCA | Ala | 3 | 7 | 6 | 1 | 4 | 13 | 1 | 1 |
| GCG | Ala | 0 | 1 | 0 | 0 | 0 | 0 | 0 | 0 |
| GAT | Asp | 4 | 5 | 25 | 27 | 3 | 6 | 4 | 2 |
| GAC | Asp | 0 | 2 | 2 | 0 | 1 | 2 | 1 | 3 |
| GAA | Glu | 10 | 6 | 21 | 3 | 6 | 12 | 9 | 6 |
| GAG | Glu | 9 | 5 | 4 | 22 | 5 | 5 | 5 | 5 |
| GGT | Gly | 2 | 1 | 8 | 4 | 0 | 0 | 0 | 0 |
| GGC | Gly | 0 | 0 | 0 | 0 | 0 | 0 | 0 | 0 |
| GGA | Gly | 2 | 1 | 6 | 3 | 1 | 0 | 1 | 0 |
| GGG | Gly | 1 | 0 | 0 | 7 | 1 | 0 | 0 | 0 |

FIG. 3A

| Codon | AA | MSP wt | Edited_MSP | MSP wt | Edited MSP | E.coli | Human |
|---|---|---|---|---|---|---|---|
| TTT | Phe | 8 | 0 | 0.53 | 0 | 0.5 | 0.35 |
| TTC | Phe | 7 | 15 | 0.47 | 1 | 0.5 | 0.65 |
| TTA | Leu | 25 | 0 | 0.66 | 0 | 0.11 | 0.05 |
| TTG | Leu | 3 | 0 | 0.08 | 0 | 0.11 | 0.09 |
| TCT | Ser | 4 | 1 | 0.17 | 0.04 | 0.27 | 0.17 |
| TCC | Ser | 2 | 3 | 0.09 | 0.13 | 0.21 | 0.26 |
| TCA | Ser | 10 | 1 | 0.43 | 0.04 | 0.13 | 0.11 |
| TCG | Ser | 0 | 0 | 0 | 0 | 0.14 | 0.07 |
| TAT | Tyr | 17 | 2 | 0.85 | 0.1 | 0.54 | 0.47 |
| TAC | Tyr | 3 | 18 | 0.15 | 0.9 | 0.46 | 0.53 |
| TAA | *** | 0 | 0 | | | | |
| TAG | *** | 0 | 0 | | | | |
| TGT | Cys | 10 | 12 | 0.83 | 1 | 0.45 | 0.3 |
| TGC | Cys | 2 | 0 | 0.17 | 0 | 0.55 | 0.7 |
| TGA | *** | 0 | 0 | | | | |
| TGG | Trp | 0 | 0 | 0 | 0 | 1 | 1 |
| CTT | Leu | 9 | 0 | 0.24 | 0 | 0.12 | 0.11 |
| CTC | Leu | 0 | 0 | 0 | 0 | 0.12 | 0.22 |
| CTA | Leu | 1 | 0 | 0.02 | 0 | 0.03 | 0.07 |
| CTG | Leu | 0 | 38 | 0 | 1 | 0.72 | 0.46 |
| CCT | Pro | 4 | 2 | 0.4 | 0.2 | 0.14 | 0.24 |
| CCC | Pro | 1 | 6 | 0.1 | 0.6 | 0.11 | 0.41 |
| CCA | Pro | 5 | 1 | 0.5 | 0.1 | 0.2 | 0.24 |
| CCG | Pro | 0 | 1 | 0 | 0.1 | 0.54 | 0.11 |
| CAT | His | 3 | 0 | 0.75 | 0 | 0.64 | 0.42 |
| CAC | His | 1 | 4 | 0.25 | 1 | 0.36 | 0.58 |
| CAA | Gln | 9 | 0 | 1 | 0 | 0.31 | 0.26 |
| CAG | Gln | 0 | 9 | 0 | 1 | 0.69 | 0.74 |
| CGT | Arg | 1 | 0 | 0.17 | 0 | 0.46 | 0.09 |
| CGC | Arg | 0 | 0 | 0 | 0 | 0.32 | 0.19 |
| CGA | Arg | 1 | 0 | 0.17 | 0 | 0.05 | 0.1 |
| CGG | Arg | 0 | 3 | 0 | 0.5 | 0.06 | 0.15 |
| ATT | Ile | 13 | 0 | 0.65 | 0 | 0.39 | 0.23 |
| ATC | Ile | 2 | 20 | 0.1 | 1 | 0.52 | 0.64 |
| ATA | Ile | 5 | 0 | 0.25 | 0 | 0.08 | 0.13 |
| ATG | Met | 3 | 3 | 1 | 1 | 1 | 1 |
| ACT | Thr | 3 | 2 | 0.19 | 0.13 | 0.36 | 0.2 |
| ACC | Thr | 3 | 13 | 0.19 | 0.81 | 0.38 | 0.47 |
| ACA | Thr | 9 | 1 | 0.56 | 0.06 | 0.09 | 0.21 |
| ACG | Thr | 1 | 0 | 0.06 | 0 | 0.17 | 0.12 |
| AAT | Asn | 29 | 3 | 0.71 | 0.07 | 0.29 | 0.34 |
| AAC | Asn | 12 | 38 | 0.29 | 0.93 | 0.71 | 0.66 |
| AAA | Lys | 38 | 0 | 0.9 | 0 | 0.72 | 0.45 |
| AAG | Lys | 4 | 42 | 0.1 | 1 | 0.28 | 0.55 |
| AGT | Ser | 5 | 2 | 0.21 | 0.09 | 0.11 | 0.11 |
| AGC | Ser | 2 | 16 | 0.09 | 0.7 | 0.14 | 0.29 |
| AGA | Arg | 4 | 3 | 0.67 | 0.5 | 0.08 | 0.24 |
| AGG | Arg | 0 | 0 | 0 | 0 | 0.03 | 0.23 |
| GTT | Val | 15 | 0 | 0.71 | 0 | 0.37 | 0.13 |
| GTC | Val | 1 | 11 | 0.05 | 0.52 | 0.12 | 0.27 |
| GTA | Val | 5 | 0 | 0.24 | 0 | 0.28 | 0.09 |
| GTG | Val | 0 | 10 | 0 | 0.48 | 0.23 | 0.5 |
| GCT | Ala | 2 | 0 | 0.22 | 0 | 0.33 | 0.31 |
| GCC | Ala | 1 | 8 | 0.11 | 0.89 | 0.18 | 0.4 |
| GCA | Ala | 6 | 1 | 0.67 | 0.11 | 0.28 | 0.17 |
| GCG | Ala | 0 | 0 | 0 | 0 | 0.21 | 0.12 |
| GAT | Asp | 25 | 27 | 0.93 | 1 | 0.48 | 0.38 |
| GAC | Asp | 2 | 0 | 0.07 | 0 | 0.52 | 0.62 |
| GAA | Glu | 21 | 3 | 0.84 | 0.12 | 0.67 | 0.4 |
| GAG | Glu | 4 | 22 | 0.16 | 0.88 | 0.33 | 0.6 |
| GGT | Gly | 8 | 4 | 0.57 | 0.29 | 0.46 | 0.15 |
| GGC | Gly | 0 | 0 | 0 | 0 | 0.4 | 0.44 |
| GGA | Gly | 6 | 3 | 0.43 | 0.21 | 0.06 | 0.17 |
| GGG | Gly | 0 | 7 | 0 | 0.5 | 0.08 | 0.24 |

FIG. 3B

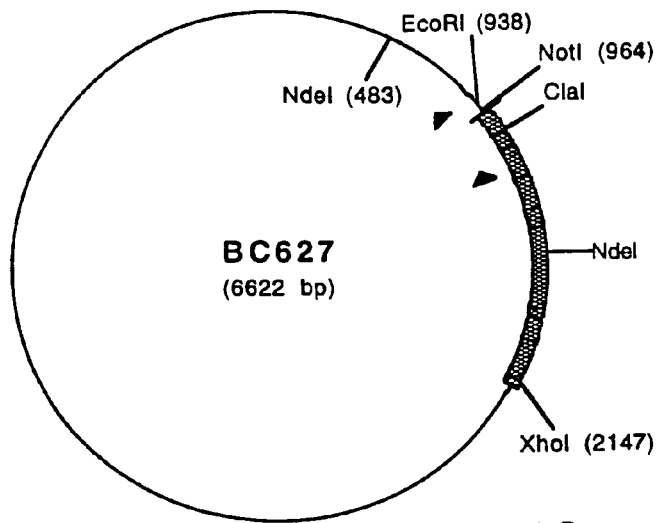

FIG. 4C

Oligos used:

OT1:
TCG ACG AGA GCC ATG AAG GTC CTC ATC CTT GCC TGT CTG GTG GCT CTG GCC ATT GCA AGA GAG CAG GAA GAA CTC AAT GTA GTC GGT A,

OT2:
GAT CTA CCG ACT ACA TTG AGT TCT TCC TGC TCT CTT GCA ATG GCC AGA GCC ACC AGA CAG GCA AGG ATG AGG ACC TTC ATG GCT CTC G,

MSP1:
AATAGATCTGCAGTAACTCCTTCCGTAATTG,

MSP2:
AATTCTCGAGTTAGTGGTGGTGGTGGTGGTGACTGCAGAAATACCATC

MSP8:
TAACTCGAGCGAACCATGAAGGTCCTCATCCTTGCCTGTCTGGTGGCTCTGGCCATTGCA

FIG. 6

PANEL A        PANEL B

Diagram of BC620

```
 36  ATGAAGGTCCTCATAATTGCCTGTCTGGTGGCTCTGGCCATTGCAGCCGTCACTCCCTCCGTCATCGATAAC
 1▶ M  K  V  L  I  I  A  C  L  V  A  L  A  I  A  A  V  T  P  S  V  I  D  N
 98  ATCCTGTCCAAGATCGAGAACGAGTACGAGGTGCTGTACCTGAAGCCCCTGGCAGGAGTCTACAGGAGCCT
25▶  I  L  S  K  I  E  N  E  Y  E  V  L  Y  L  K  P  L  A  G  V  Y  R  S  L
169  GAAGAAGCAGCTGGAGAACAACGTGATGACCTTCAACGTGAACGTGAAGGATATCCTGAACAGCAGGTTCAA
48▶  K  K  Q  L  E  N  N  V  M  T  F  N  V  N  V  K  D  I  L  N  S  R  F  N
241  CAAGAGGGAGAACTTCAAGAACGTGCTGGAGAGCGATCTGATCCCCTACAAGGATCTGACCAGCAGCAACTA
72▶  K  R  E  N  F  K  N  V  L  E  S  D  L  I  P  Y  K  D  L  T  S  S  N  Y
                             EcoNI (337)
313  CGTGGTCAAAGATCCCTACAAGTTCCTGAACAAGGAGAAGAGAGATAAGTTCCTGAGCAGTTACAATTACAT
                             ──────────▶
96▶  V  V  K  D  P  Y  K  F  L  N  K  E  R  D  K  F  L  S  S  Y  N  Y  I
385  CAAGGATAGCATTGACACCGATATCAACTTCGCCAACGATGTCCTGGATACTACAAGATCCTGTCCGAGAA
120▶ K  D  S  I  D  T  D  I  N  F  A  N  D  V  L  G  Y  Y  K  I  L  S  E  K
457  GTACAAGAGCGATCTGGATAGCATCAAGAAGTACATCAACGATAAGCAGGGAGAGAACGAGAAGTACCTGCC
144▶ Y  K  S  D  L  D  S  I  K  K  Y  I  N  D  K  Q  G  E  N  E  K  Y  L  P
529  CTTCCTGAACAACATCGAGACCCTGTACAAGACCGTCAACGATAAGATTGATCTGTTCGTGATCCACCTGGA
168▶ F  L  N  N  I  E  T  L  Y  K  T  V  N  D  K  I  D  L  F  V  I  H  L  E
              NdeI (621)
601  GGCCAAGGTCCTGCAGTACACATATGAGAAGAGCAACGTGGAGGTCAAGATCAAGGAGCTGAATTACCTGAA
                ◀──────────
192▶ A  K  V  L  Q  Y  T  Y  E  K  S  N  V  E  V  K  I  K  E  L  N  Y  L  K
673  GACCATCCAGGATAAGCTGGCCGATTTCAAGAAGAACAACAACTTCGTCGGAATCGCCGATCTGAGCACCGA
216▶ T  I  Q  D  K  L  A  D  F  K  K  N  N  N  F  V  G  I  A  D  L  S  T  D
745  TTACAACCACAACAACCTGCTGACCAAGTTCCTGAGCACCGGAATGGTCTTCGAAAACCTGGCCAAGACCGT
240▶ Y  N  H  N  N  L  L  T  K  F  L  S  T  G  M  V  F  E  N  L  A  K  T  V
                           BsmI (849)
817  CCTGAGCAACCTGCTGGATGGAAACCTGCAGGGAATGCTGCAGATCAGCCAGCACCAGTGTGTGAAGAAGC
                           ──────────▶
264▶ L  S  N  L  L  D  G  N  L  Q  G  M  L  Q  I  S  Q  H  Q  C  V  K  K
888  AGTGTCCCCAGAACAGCGGATGCTTCAGACACCTGGATGAGAGGAGGAGTGCAAGTGCCTGCTGAACTA
288▶ Q  C  P  Q  N  S  G  C  F  R  H  L  D  E  R  E  E  C  K  C  L  L  N  Y
958  CAAGCAGGAAGGAGATAAGTGTGTGTGGAAAACCCCAATCCTACTTGTAACGAGAACAATGGAGGATGCGATG
311▶ K  Q  E  G  D  K  C  V  E  N  P  N  P  T  C  N  E  N  N  G  G  C  D
1029 CCGATGCCAAGTGTACCGAGGAGGATTCAGGAAGCAACGGAAAGAAGATCACCTGCGAGTGTACCAAGCCT
335▶ A  D  A  K  C  T  E  E  D  S  G  S  N  G  K  K  I  T  C  E  C  T  K  P
                                                         XhoI (1157)
1100 GATTCTTATCCACTGTTCGATGGtAtCTTCTGCAGTCACCACCACCACCACCACTAACTCGAGGAT
                                             ◀──────────
359▶ D  S  Y  P  L  F  D  G  I  F  C  S  H  H  H  H  H  H  •  L  E  D
```

FIG. 11

MEROZOITE SURFACE PROTEIN 1 LACKING GLYCOSYLATION SITES

CROSS-REFERENCE TO RELATED APPLICATIONS

This application is a division of U.S. patent application Ser. No. 10/082,018, filed on Feb. 20, 2002, now abandoned which is a continuation of U.S. patent application Ser. No. 09/175,684, filed Oct. 20, 1998 now U.S. Pat. No. 6,593,463, which in turn claims the benefit of 60/085,649, filed May 15, 1998 and claims the benefit of 60/062,592, filed Oct. 20, 1997, the contents of which are incorporated in their entirety.

BACKGROUND OF THE INVENTION

1. Field of the Invention

The invention relates to heterologous gene expression. More particularly, the invention relates to the expression of malaria genes in higher eukaryote cell systems.

2. Summary of the Related Art

Recombinant production of certain heterologous gene products is often difficult in in vitro cell culture systems or in vivo recombinant production systems. For example, many researchers have found it difficult to express proteins derived from bacteria, parasites and virus in cell culture systems different from the cell from which the protein was originally derived, and particularly in mammalian cell culture systems. One example of a therapeutically important protein which has been difficult to produce by mammalian cells is the malaria merozoite surface protein (MSP-1).

Malaria is a serious heath problem in tropical countries. Resistance to existing drugs is fast developing and a vaccine is urgently needed. Of the number of antigens that get expressed during the life cycle of *P. falciparum*, MSP-1 is the most extensively studied and promises to be the most successful candidate for vaccination. Individuals exposed to *P. falciparum* develop antibodies against MSP-1, and studies have shown that there is a correlation between a naturally acquired immune response to MSP-1 and reduced malaria morbidity. In a number of studies, immunization with purified native MSP-1 or recombinant fragments of the protein has induced at least partial protection from the parasite (Diggs et al, (1993) *Parasitol. Today* 9:300-302). Thus MSP-1 is an important target for the development of a vaccine against *P. falciparum*.

MSP-1 is a 190-220 kDA glycoprotein. The C-terminal region has been the focus of recombinant production for use as a vaccine. However, a major problem in developing MSP-1 as a vaccine is the difficulty in obtaining recombinant proteins in bacterial or yeast expression systems that are equivalent in immunological potency to the affinity purified native protein (Chang et al., (1992) *J. Immunol.* 148:548-555.) and in large enough quantities to make vaccine production feasible.

Improved procedures for enhancing expression of sufficient quantities of MSP-1 would be advantageous.

BRIEF SUMMARY OF THE INVENTION

The present invention provides improved recombinant DNA compositions and procedures for increasing the mRNA levels and protein expression of the malarial surface antigen MSP-1 in cell culture systems, mammalian cell culture systems, or in transgenic mammals. The preferred protein candidate for expression in an expression system in accordance with the invention is a C-terminal derivative of MSP-1 having a DNA coding sequence with reduced AT content, and eliminated mRNA instability motifs and rare codons relative to the recombinant expression systems. Thus, in a first aspect, the invention provides a DNA sequence derived from the sequence shown in SEQ ID NO 2. This derivative sequence is shown in SEQ ID NO 1.

In a second aspect, the invention provides a process for preparing a modified nucleic acid of the invention comprising the steps of lowering the overall AT content of the natural gene encoding MSP-1, eliminating all mRNA instability motifs and replacing all rare codons with a preferred codon of the mammary gland tissue, all by replacing specific codons in the natural gene with codons recognizable to, and preferably preferred by mammary gland tissue and which code for the same amino acids as the replaced codon. This aspect of the invention further includes modified nucleic acids prepared according to the process of the invention.

In a third aspect, the invention also provides vectors comprising modified MSP-1 nucleic acids of the invention and a goat beta casein promoter and signal sequence, and host cells transformed with nucleic acids of the invention.

In a fourth aspect, the invention provides transgenic non-human mammals whose germlines comprise a nucleic acid of the invention.

In a fifth aspect, the invention provides a DNA vaccine comprising a modified MSP-1 gene according to the invention.

DESCRIPTION OF THE DRAWINGS

FIG. 1 depicts the cDNA sequence of MSP-1$_{42}$ modified in accordance with the invention [SEQ ID NO 1] in which 306 nucleotide positions have been replaced to lower AT content and eliminate mRNA instability motifs while maintaining the same protein amino acid sequence of MSP-1$_{42}$. The large letters indicate nucleotide substitutions.

FIG. 2 depicts the nucleotide sequence coding sequence of the "wild type" or native MSP-1$_{42}$ [SEQ ID NO 2].

FIG. 3 is a codon usage table for wild type MSP-1$_{42}$ (designated "MSP wt" in the table) and the new modified MSP-1$_{42}$ gene (designated "edited MSP" in the table) and several milk protein genes (casein genes derived from goats and mouse). The numbers in each column indicate the actual number of times a specific codon appears in each of the listed genes. The new MSP-1$_{42}$ synthetic gene was derived from the mammary specific codon usage by first choosing GC rich codons for a given amino acid combined with selecting the amino acids used most frequently in the milk proteins.

FIG. 4a-c depict MSP-1$_{42}$ constructs GTC 479, GTC 564, and GTC 627, respectively as are described in the examples.

FIG. 6 depicts the nucleic acid sequences of OT1 [SEQ ID NO 3], OT2 [SEQ ID NO 4], MSP-8 [SEQ ID ON 5], MSP-2 [SEQ ID NO 6]and MSP1 [SEQ ID NO 7] described in the Examples.

FIG. 11 is a schematic representation of the nucleotide sequence of MSP42-2 [SEQ ID NO 8].

DETAILED DESCRIPTION OF THE PREFERRED EMBODIMENTS

Figure 4A:
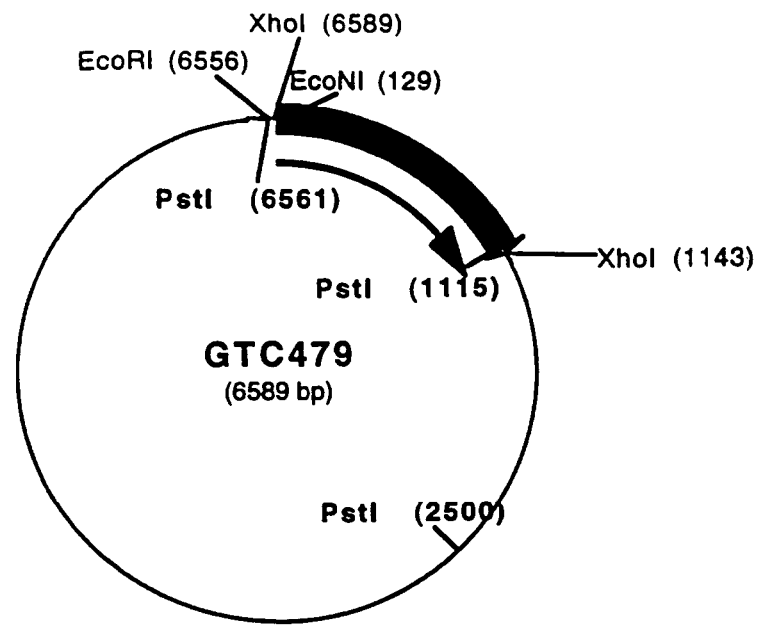

The patent and scientific literature referred to herein establishes the knowledge that is available to those with skill in the art. The issued US patents, allowed applications, published foreign applications, and references cited herein are hereby incorporated by reference. Any conflicts between these references and the present disclosure shall be resolved in favor of the present disclosure.

The present invention provides improved recombinant DNA compositions and procedures for increasing the mRNA levels and protein expression of the malarial surface antigen MSP-1 in cell culture systems, mammalian cell culture systems, or in transgenic mammals. The preferred protein candidate for expression in an expression system in accordance with the invention is a C-terminal derivative of MSP-1 having a DNA coding sequence with reduced AT content, and eliminated mRNA instability motifs and rare codons relative to the recombinant expression systems. Thus, in a first aspect, the invention provides a DNA sequence derived from the sequence shown in SEQ ID NO 2. This derivative sequence is shown in SEQ ID NO 1.

In preferred embodiments, the nucleic acid of the invention is capable of expressing MSP-1 in mammalian cell culture systems, or in transgenic mammals at a level which is at least 25%, and preferably 50% and even more preferably at least 100% or more of that expressed by the natural gene in mammalian cell culture systems, or in transgenic mammals under identical conditions.

As used herein, the term "expression" is meant mRNA transcription resulting in protein expression. Expression may be measured by a number of techniques known in the art including using an antibody specific for the protein of interest. By "natural gene" or "native gene" is meant the gene sequence, or fragments thereof (including naturally occurring allelic variations), which encode the wild type form of MSP-1 and from which the modified nucleic acid is derived. A "preferred codon" means a codon which is used more prevalently by the cell or tissue type in which the modified MSP-1 gene is to be expressed, for example, in mammary tissue. Not all codon chances described herein are changes to a preferred codon, so long as the codon replacement is a codon which is at least recognized by the mouse mammary tissue. The term "reduced AT content" as used herein means having a lower overall percentage of nucleotides having A (adenine) or T (thymine) bases relative to the natural MSP-1 gene due to replacement of the A or T containing nucleotide positions or A and/or T containing codons with nucleotides or codons recognized by mouse mammary tissue and which do not change the amino acid sequence of the target protein.

In a second aspect, the invention provides a process for preparing a modified nucleic acid of the invention comprising the steps of lowering the overall AT content of the natural gene encoding MSP-1, eliminating all mRNA instability motifs and replacing all rare codons with a preferred codon of mammary gland tissue, all by replacing specific codons in the natural gene with codons recognizable to, and preferably preferred by mammary gland tissue and which code for the same amino acids as the replaced codon. Standard reference works describing the general principals of recombinant DNA technology include Watson, J. D. et al, *Molecular Biology of the Gene*, Volumes I and II the Benjamin/Cummings Publishing Company, Inc. publisher, Menlo Park, Calif. (1987) Darnell, J. E. et al., *Molecular Cell Biology*, Scientific American Books, Inc., Publisher, New York, N.Y. (1986); Old, R. W., et al., *Principles of Gene Manipulation: An Introduction to Genetic Engineering*, 2d edition, University of California Press, publisher, Berkeley Calif. (1981); Maniatis, T., et al., *Molecular Cloning: A Laboratory Manual*, $2^{nd}$ ed. Cold Spring Harbor Laboratory, publisher, Cold Spring Harbor, N.Y. (1989) and *Current Protocols in Molecular Biology*, Ausubel et al., Wiley Press, New York, N.Y. (1992). This aspect of the invention further includes modified nucleic acids prepared according to the process of the invention.

Without being limited to any theory, previous research has indicated that a conserved AU sequence (AUUUA) from the 3' untranslated region of GM-CSF mRNA mediates selective mRNA degradation (Shaw, G. and Kamen, R. *Cell* 46:659-667). The focus in the past has been on the presence of these instability motifs in the untranslated region of a gene. The instant invention is the first to recognize an advantage to eliminating the instability sequences in the coding region of the MSP-1 gene.

In a third aspect, the invention also provides vectors comprising modified MSP-1 nucleic acids of the invention and a goat beta casein promoter and signal sequence, and host cells transformed with nucleic acids of the invention.

In a fourth aspect, the invention provides transgenic non-human mammals whose germlines comprise a nucleic acid of the invention. General principals for producing transgenic animals are known in the art. See for example Hogan et al., *Manipulating the Mouse Embryo: A Laboratory Manual*, Cold Spring Harbor Laboratory, (1986); Simons et al, *Bio/Technology* 6:179-183, (1988); Wall et al., *Biol. Reprod.* 32:645-651, (1985); Buhler et al., *Bio/Technology*, 8:140-143 (1990); Ebert et al., *Bio/Technology* 9:835-838 (1991); Krimenfort et al., *Bio/Technology* 9:844-847 (1991); Wall et al., *J. Cell. Biochem.* 49:113-120 (1992). Techniques for introducing foreign DNA sequences into mammals and their germ cells were originally developed in the mouse. See e.g., Gordon et al., *Proc. Natl. Acad. Sci. USA* 77:7380-7384, (1980); Gordon and Ruddle, Science 214: 1244-1246 (1981); Palmiter and Brinster, *Cell* 41: 343-345, 1985; Brinster et al., *Proc Natl. Acad. Sci., USA* 82:4438-4442 (1985) and Hogan et al. (*ibid.*). These techniques were subsequently adapted for use with larger animals including cows and goats. Up until very recently, the most widely used procedure for the generation of transgenic mice or livestock, several hundred linear molecules of the DNA of interest in the form of a transgenic expression construct are injected into one of the pro-nuclei of a fertilized egg. Injection of DNA into the cytoplasm of a zygote is also widely used. Most recently cloning of an entire transgenic cell line capable of injection into an unfertilized egg has been achieved (KHS Campbell et al., *Nature* 380 64-66, (1996)).

The mammary gland expression system has the advantages of high expression levels, low cost, correct processing and accessibility. Known proteins, such as bovine and human alpha-lactalbumin have been produced in lactating transgenic animals by several researchers. (Wright et al, Bio/Technology 9:830-834 (1991); Vilotte et al, Eur. J. Biochem., 186:43-48 (1989); Hochi et al., Mol Reprod. And Devel. 33:160-164 (1992); Soulier et al., FEBS Letters 297(1,2):13-18 (1992)) and the system has been shown to produce high levels of protein.

In a fifth aspect, the invention provides a DNA vaccine comprising a modified MSP-1 gene according to the invention. Such DNA vaccines may be delivered without encapsulation, or they may be delivered as part of a liposome, or as part of a viral genome. Generally, such vaccines are delivered in an amount sufficient to allow expression of the modified MSP-1 gene and to elicit an antibody response in an animal, including a human, which receives the DNA vaccine. Subsequent deliveries, at least one week after the first delivery, may be used to enhance the antibody response. Preferred delivery routes include introduction via mucosal membranes, as well as parenteral administration.

EXAMPLES

Creation of Novel Modified MSP-$1_{42}$ Gene

A novel modified nucleic acid encoding the C-terminal fragment of MSP-1 is provided. The novel, modified nucleic acid of the invention encoding a 42 kD C-terminal part of MSP-1 (MSP-$1_{42}$) capable of expression in mammalian cells of the invention is shown in FIG. 1. The natural MSP-$1_{42}$ gene (FIG. 2) was not capable of being expressed in mammalian cell culture or in transgenic mice Analysis of the natural MSP-142 gene suggested several characteristics that distinguish it from mammalian genes. First, it has a very high overall AT content of 76%. Second, the mRNA instability motif, AUUUA, occurred 10 times in this 1100 bp DNA segment (FIG. 2). To address these differences a new MSP-$1_{42}$ gene was designed. Silent nucleotide substitution was introduced into the native MSP-$1_{42}$ gene at 306 positions to reduce the overall AT content to 49.7%. Each of the 10 AUUUA mRNA instability motifs in the natural gene were eliminated by changes in codon usage as well. To change the codon usage, a mammary tissue specific codon usage table, FIG. 3a, was created by using several mouse and goat mammary specific proteins. The table was used to guide the choice of codon usage for the modified MSP-$1_{42}$ gene as described above. For example as shown in the Table in FIG. 3a, in the natural gene, 65% (25/38) of the Leu was encoded by TTA, a rare codon in the mammary gland. In the modified MSP-$1_{42}$ gene, 100% of the Leu was encoded by CTG, a preferred codon for Leu in the mammary gland.

An expression vector was created using the modified MSP-$1_{42}$ gene by fusing the first 26 amino acids of goat beta-casein to the N-terminal of the modified MSP-$1_{42}$ gene and a SalI-Xho I fragment which carries the fusion gene was subcloned into the XhoI site of the expression vector pCDNA3. A His6 tag was fused to the 3' end of the MSP-$1_{42}$ gene to allow the gene product to be affinity purified. This resulted in plasmid GTC627 (FIG. 4c).

To compare the natural MSP-$1_{42}$ gene construct to the modified MSP-$1_{42}$ nucleic acid of the invention, an expression vector was also created for the natural MSP-$1_{42}$ gene and the gene was added to mammalian cell culture and injected into mice to form transgenic mice as follows:

Construction of the Native MSP-$1_{42}$ Expression Vector

Figure 4B:
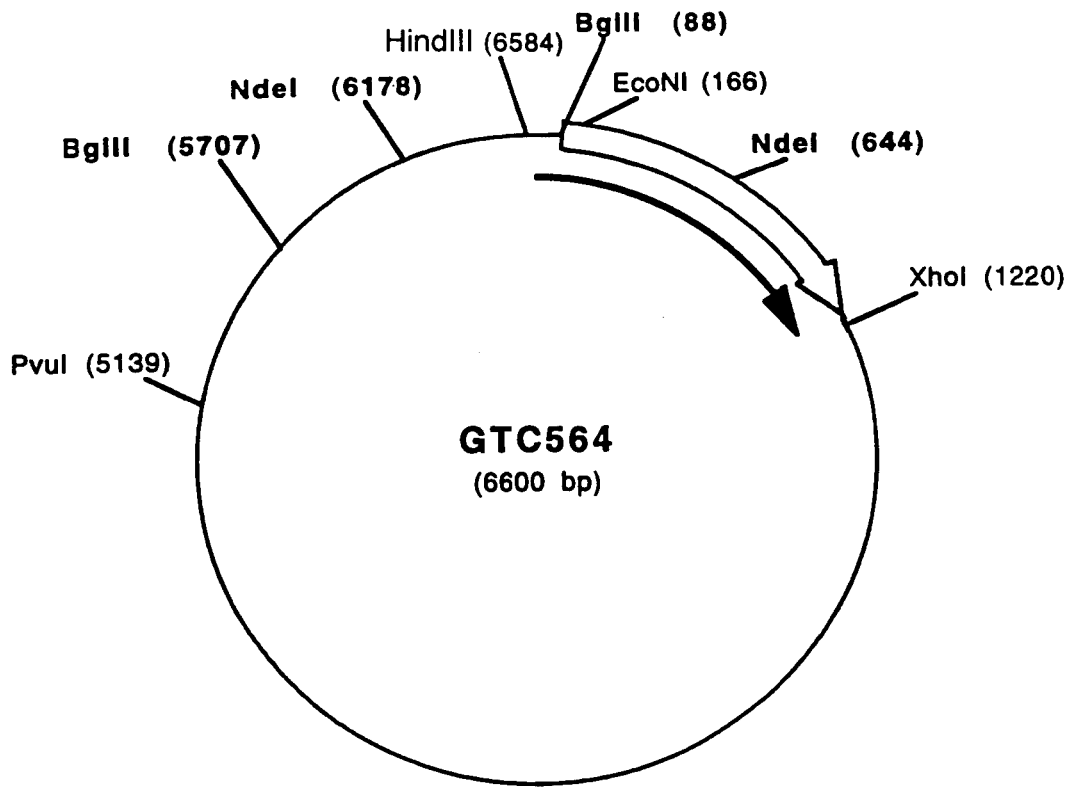

To secrete the truncated merozoite surface protein-1 (MSP-1) of Plasmodium falciparum, the wild type gene encoding the 42 KD C-terminal part of MSP-1 (MSP-$1_{42}$) was fused to either the DNA sequence that encodes the first 15 or the first 26 amino acids of the goat beta-casein. This is achieved by first PCR amplify the MSP-1 plasmid (received from Dr. David Kaslow, N1H) with primers MSP1 and MSP2 (FIG. 6), then cloned the PCR product into the TA vector (Invitrogen). The BglII-XhoI fragments of the PCR product was ligated with oligos OT1 and OT2 (FIG. 6) into the expression vector pCDNA3. This yielded plasmid GTC564 (FIG. 4b), which encodes the 15 amino acid beta-casein signal peptide and the first 11 amino acids of the mature goat beta-casein followed by the native MSP-$1_{42}$ gene. Oligos MSP-8 and MSP-2 (FIG. 6) were used to amplify MSP-1 plasmid by PCR, the product was then cloned into TA vector. The XhoI fragment was exercised and cloned into the XhoI site of the expression vector pCDNA3 to yield plasmid GTC479 (FIG. 4a), which encoded 15 amino acid goat beta-casein signal peptide fused to the wild-type MSP-$1_{42}$ gene. A His6 tag was added to the 3' end of MSP-$1_{42}$ gene in GTC 564 and GTC 479.

Native MSP-$1_{42}$ Gene Is Not Expressed In COS-7 Cells

Expression of the native MSP gene in cultured COS-7 cells was assayed by transient transfection assays. GTC479 and GTC564 plasmids DNA were introduced into COS-7 cells by lipofectamine (Gibco-BRL) according to manufacturer's protocols. Total cellular RNA was isolated from the COS cells two days post-transfection. The newly synthesized proteins were metabolically labeled for 10 hours by adding $^{35}S$ methionine added to the culture media two days-post transfection.

To determine the MSP mRNA expression in the COS cells, a Northern blot was probed with a $^{32}P$ labeled DNA fragment from GTC479. No MSP RNA was detected in GTC479 or GTC564 transfectants (data not shown). Prolonged exposure revealed residual levels of degraded MSP mRNA. The $^{35}S$ labeled culture supernatants and the lysates were immunoprecipitated with a polyclonal antibody raised against MSP. Immunoprecipitation experiments showed that no expression from either the lysates or the supernatants of the GTC479 or GTC564 transfected cells (data not shown). These results showed that the native MSP-1 gene was not expressed in COS cells.

Figure 7:
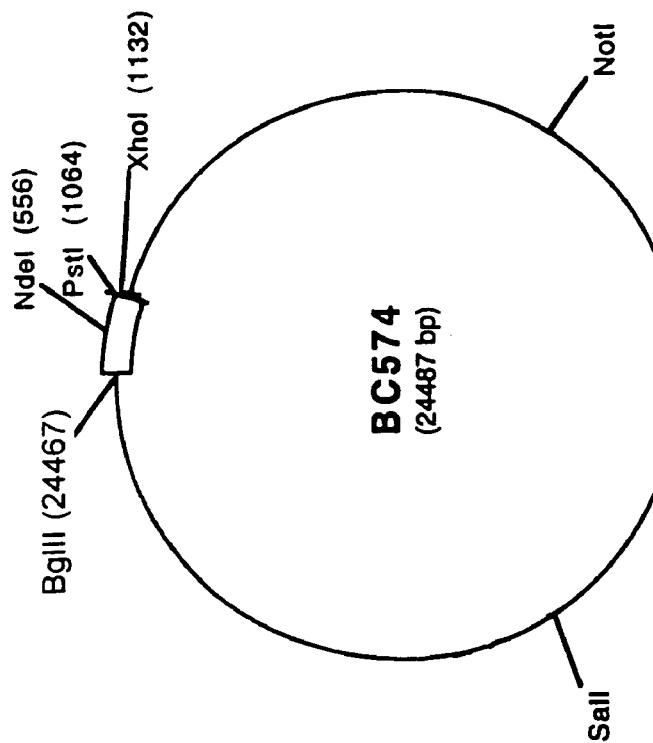
FIG. 7 is a schematic representation of plasmid BC574.

Native MSP-$1_{42}$ Gene is Not Expressed in the Mammary Gland of Transgenic Mice The SalI-XhoI fragment of GTC479, which encoded the 15 amino acids of goat beta-casein signal peptide, the first 11 amino acids of goat beta-casein, and the native MSP-$1_{42}$ gene, was cloned into the XhoI site of the beta-casein expressed in vector BC350. This yielded plasmid BC574 (FIG. 7). A SalI-NotI fragment of BC574 was injected into the mouse embryo to generate transgenic mice. Fifteen lines of transgenic mice were established. Milk from the female founder mice was collected and subjected to Western analysis with polycolonal antibodies against MSP. None of the seven mice analyzed were found to express MSP-$1_{42}$ protein in their milk. To further determine if the mRNA of MSP-$1_{42}$ was expressed in the mammary gland, total RNA was extracted from day 11 lactating transgenic mice and analyzed by Northern blotting. No MSP-$1_{42}$ mRNA was detected by any of the BC 574 lines analyzed. Therefore, the MSP-$1_{42}$ transgene was not expressed in the mammary gland of transgenic mice. Taken together, these experiments suggest that native parasitic MSP-$1_{42}$ gene could not be expressed in mammalian cells, and the block is as the level of mRNA abundance.

Expression of MSP in Tile Mammalian Cells

Figure 5:
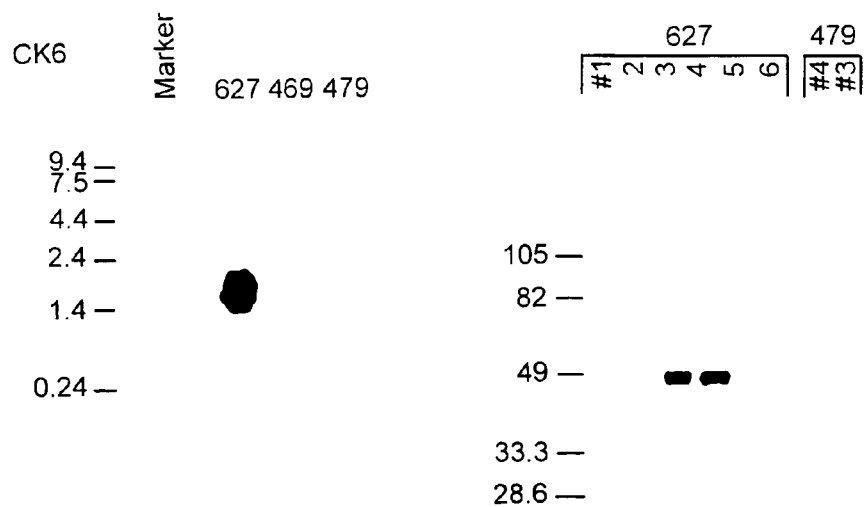
FIG. 5 panel A is a Northern analysis wherein construct GTC627 comprises the new MSP-1$_{42}$ gene modified in accordance with the invention, GTC479 is the construct comprising the native MSP-1$_{42}$ gene, and construct GTC469 is a negative control DNA FIG. 5 panel B is a Western analysis wherein the eluted fractions after affinity purifications numbers are collected fractions. The results show that fractions from GTC679 the modified MSP-1$_{42}$ synthetic gene construct reacted with polyclonal antibodies to MSP-1 and the negative control GTC479 did not.

Transient transfection experiments were performed to evaluate the expression of the modified MSP-$1_{42}$ gene of the invention in COS cells. GTC627 and GTC479 DNA were introduced into the COS-7 cells. Total RNA was isolated 48 hours post-transfection for Northern analysis. The immobilized RNA was probed with $^{32}$P labeled SalI-XhoI fragment of GTC627. A dramatic difference was observed between GTC479 and GTC627. While no MSP-142 mRNA was detected in the GTC479 transfected cells as shown previously, abundant MSP-1$_{42}$ mRNA was expressed by GTC627 (FIG. 5, Panel A). GTC 469 was used as a negative control and comprises the insert of GTC564 cloned into cloning vector PU19, a commercially available cloning vector. A metabolic labeling experiment with $^{35}$S methionine followed by immunoprecipitation with polyclonal antibody (provided by D. Kaslow NIAD, NIH) against MSP showed that MSP-1$_{42}$ protein was synthesized by the transfected COS cells (FIG. 5, Panel B). Furthermore, MSP-1$_{42}$ was detected in the transfected COS supernatant, indicating the MSP-1$_{42}$ protein was also secreted. Additionally, using Ni-NTA column, MSP-1$_{42}$ was affinity purified from the GTC627 transfected COS supernatant.

These results demonstrated that the modification of the parasitic MSP-1$_{42}$ gene lead to the expression of MSP mRNA in the COS cells. Consequently, the MSP-1$_{42}$ product was synthesized and secreted by mammalian cells.

Polyclonal antibodies used in this experiment may also be prepared by means well known in the art (*Antibodies: A Laboratory Manual*, Ed Harlow and David Lane, eds. Cold Spring Harbor Laboratory, publishers (1988)). Production of MSP serum antibodies is also described in Chang et al., *Infection and Immunity* (1996) 64:253-261 and Chang et al., (1992) *Proc Natl. Acad. Sci. USA* 86:6343-6347.

The results of this analysis indicate that the modified MSP-1$_{42}$ nucleic acid of the invention is expressed at a very high level compared to that of the natural protein which was not expressed at all. These results represent the first experimental evidence that reducing the AT % in a gene leads to expression of the MSP gene in heterologous systems and also the first evidence that removal of AUUUA mRNA instability motifs from the MSP coding region leads to the expression of MSP protein in COS cells. The results shown in FIG. 5, Panel A Northern (i.e. no RNA with native gene and reasonable levels with a modified DNA sequence in accordance with the invention), likely explains the increase in protein production.

The following examples describe the expression of MSP1-42 as a native non-fusion (and non-glycosylated) protein in the milk of transgenic mice.

Construction of MSP Transgene

Figure 8:
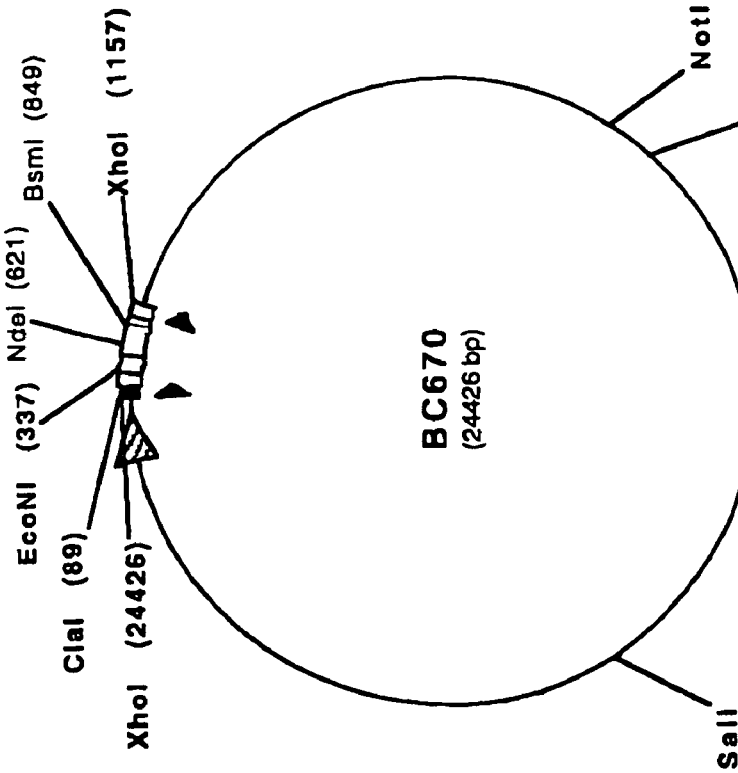
FIG. 8 is a schematic representation of BC620.
Figure 9:
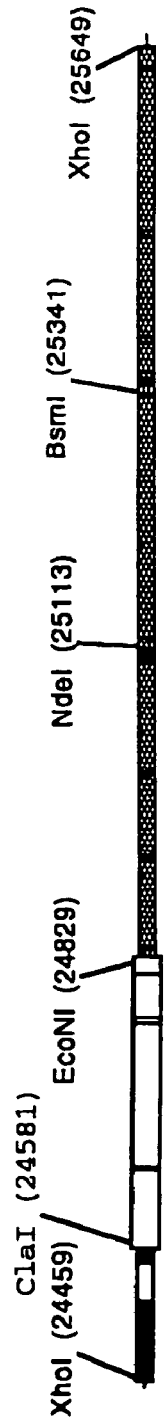
FIG. 9 is a schematic representation of BC670.

To fuse MSP1-42 to the 15 amino acid β-casein signal peptide, a pair of oligos, MSP203 and MSP204 (MSP203: ggccgctcgacgccaccatgaacctcctcataattgcc tgtctggtggctctggc-cattgcagccgtcactccctccgtcat, MSP204: cgatgacggagggagt-gacggctg caatggccagagccaccagacaggcaat-tatgaggaccttcatggtggcgtcgagc), which encode the 15 amino acid—casein signal and the first 5 amino acid of the MSP 1-42 ending at the Cla I site, was ligated with a Cla I-Xho I fragment of BC620 (FIG. 8) which encodes the rest of the MSP1-42 gene, into the Xho I site of the expression vector pcDNA3. A Xho I fragment of this plasmid (GTC669) was then cloned into the Xho I site of milk specific expression vector BC350 to generate B670 (FIG. 9)

Expression of MSP1-42 in the Milk of Transgenic Mice

Figure 10:
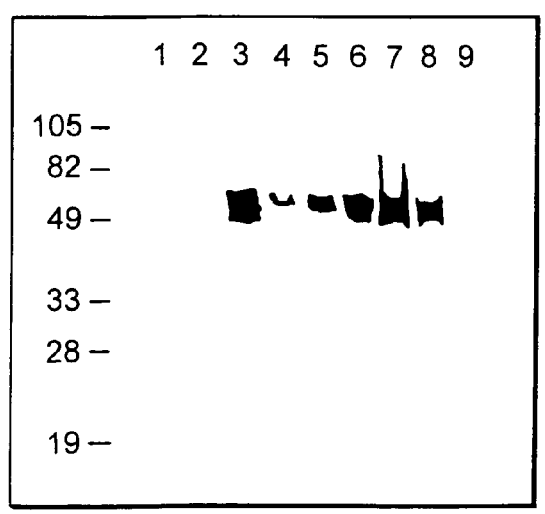
FIG. 10 is a representation of a Western blot of MSP transgenic milk.

A Sal I-Not I fragment was prepared from plasmid BC670 and microinjected into the mouse embryo to generate transgenic mice. Transgenic mice was identified by extracting mouse DNA from tail biopsy followed by PCR analysis using oligos GTC17 and MSP101 (sequences of oligos: GTC17, GATTGACAAGTAATACGCTGTTTCCTC, Oligo MSP101. GGATTCAATAGATACGG). Milk from the female founder transgenic mice was collected at day 7 and day 9 of lactation, and subjected to western analysis to determine the expression level of MSP-1-42 using an polyclonal anti-MSP antibody and monoclonal anti MSP antibody 5.2 (Dr. David Kaslow, N1H). Results indicated that the level of MSP-1-42 expression in the milk of transgenic mice was at 1-2 mg/ml (FIG. 10).

Construction of MSP1-42 Glycosylation Site Minus Mutants

Our analysis of the milk produced MSP revealed that the transgenic MSP protein was N-glycosylated. To eliminate the N-glycosylation sites in the MSP1-42 gene, Asn. (N) at positions 181 and 262 were substituted with Gln.(Q). The substitutions were introduced by designing DNA oligos that anneal to the corresponding region of MSP1 and carry the AAC to CAG mutations. These oligos were then used as PCR primers to produce DNA fragments that encode the N to Q substitutions.

To introduce N262-Q mutation, a pair of oligos, MSPGY-LYCO-3 (CAGGGAATGCTGCAGATCAGC) AND MSP42-2 (AATTCTCGAGTTAGTG GTGGTGGTGGTG-GTGATCGCAGAAAATACCATG, FIG. 11), were used to PCR amplify plasmid GTC627, which contains the synthetic MSP1-42 gene. The PCR product was cloned into pCR2.1 vector (Invitrogen). This generated plasmid GTC716.

To introduce N181-Q mutation, oligos MSPGLYCO-1 (CTCCTTGTTCAGG AACTTGTAGGG) and MSPGLCO-2 (GTCCTGCAGTACACATATGAG, FIG. 4) were used to amplify plasmid GTC 627. The PCR product was cloned into pCR2.1. This generated plasmid GTC700.

Figure 12:
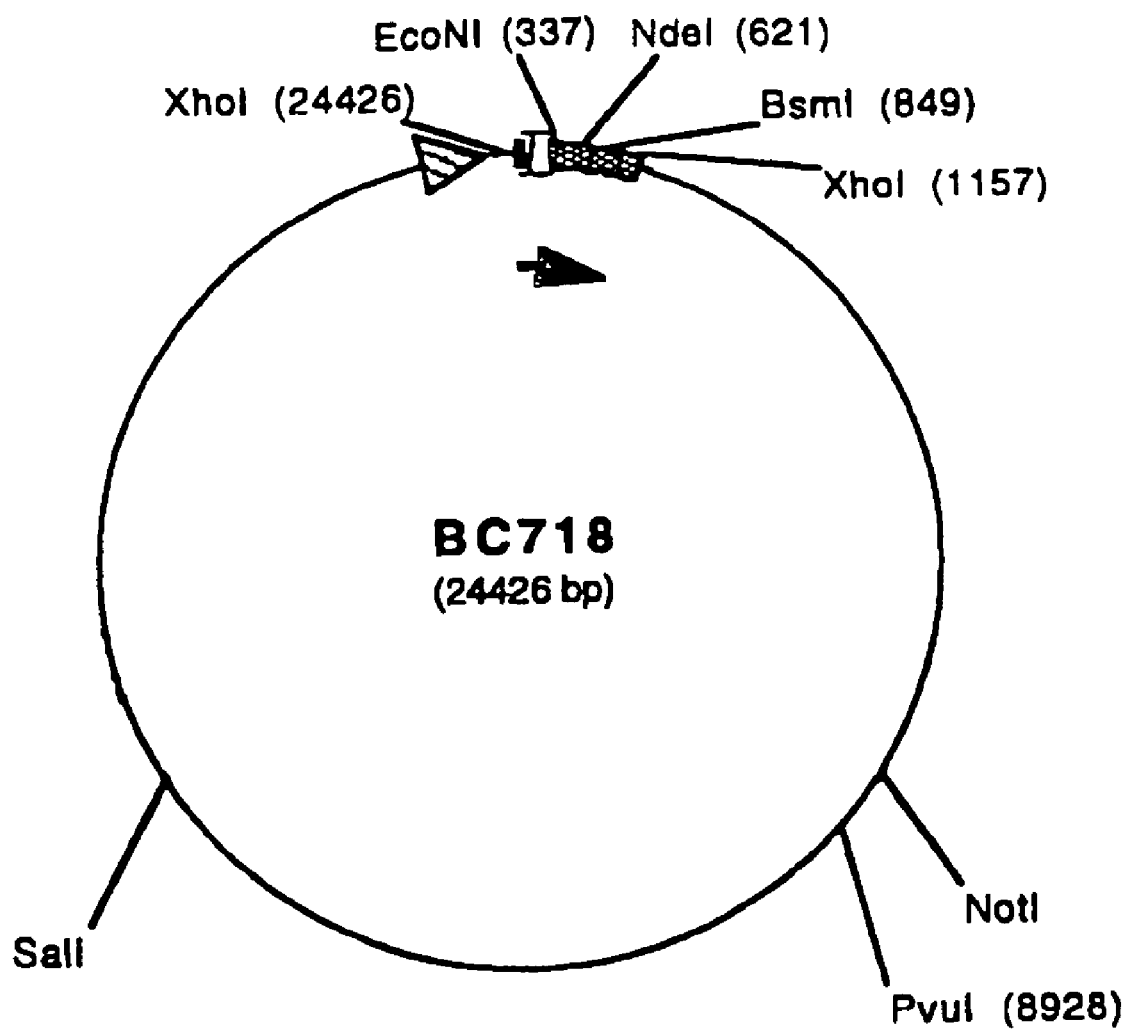
FIG. 12 is a schematic representation of the BC-718.

The MSP double glycosylation mutant was constructed by the following three steps: first, a Xho I-Bsm I fragment of BC670 and the Bsm I-Xho I fragment of GTC716 is ligated into the Xho I site of vector pCR2.1. This resulted a plasmid that contain the MSP-1-42 gene with N262-Q mutation. EcoN I-Nde I fragment of this plasmid was then replaced by the EcoN I-Nde I fragment from plasmid GTC716 to introduce the second mutation, N181-Q. A Xho I fragment of this plasmid was finally cloned into BC350 to generate BC718 (FIG. 12).

Transgenic Expression of Nonglycosylated MSP-1

BC718 has the following characteristics: it carries the MSP1-42 gene under the control of the β-casein promoter so it can be expressed in the mammary gland of the transgenic animal during lactation. Further, it encodes a 15 amino acid B-casein leader sequence fused directly to MSP1-42 so that the MSP1-42, without any additional amino acid at its N-terminal, can be secreted into the milk. Finally, because the N-Q substitutions, the MSP produced in the milk of the transgenic animal by this construct will not be N-glycosylated. Taken together, the transgenic MSP produced in the milk by BC718 is the same as the parasitic MSP.

Figure 13:
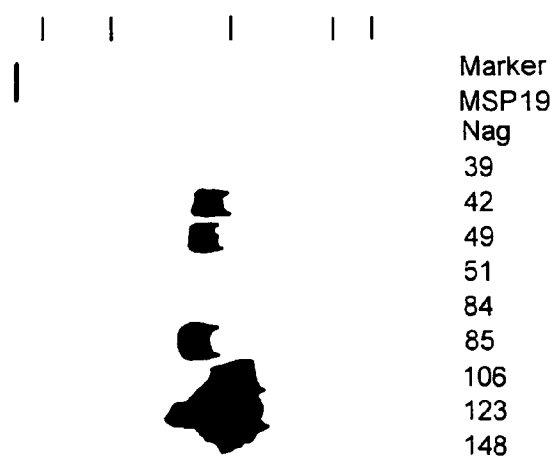
FIG. 13 is a representation of a Western blot of BC-718 expression in transgenic milk.

A SAlI/XhoI fragment was prepared from plasmid BC718 and microinjected into mouse embryos to generate transgenic mice. Transgenic animals were identified as described previously. Milk from female founders was collected and analyzed by Western blotting with antibody 5.2. The results, shown in FIG. 13, indicate expression of nonglycosylated MSP1 at a concentration of 0.5 to 1 mg/ml.

What is claimed is:

1. A composition comprising a merozoite surface protein 1 (MSP-1) or fragment thereof, wherein at least one glycosylation site of the merozoite surface protein 1 (MSP-1) or fragment thereof has been eliminated.

2. A composition comprising a merozoite surface protein 1 (MSP-1) or fragment thereof, wherein all of the glycosylation sites of the merozoite surface protein 1 (MSP-1) or fragment thereof have been eliminated.

3. The composition of claim 1 or 2, wherein the sequence of the MSP-1 is as set forth in SEQ ID NO: 9, but wherein the glycosylation site at position 182 has been eliminated by an amino acid substitution at position 182.

4. The composition of claim 1 or 2, wherein the sequence of the MSP-1 is as set forth in SEQ ID NO: 9, but wherein the glycosylation site at position 263 has been eliminated by an amino acid substitution at position 263.

5. The composition of claim 1 or 2, wherein the sequence of the MSP-1 is as set forth in SEQ ID NO: 9, but wherein the glycosylation sites at positions 182 and 263 have been eliminated by amino acid substitutions at positions 182 and 263.

6. A composition comprising a merozoite surface protein 1 (MSP-1) or fragment thereof produced by:
providing a non-human transgenic mammal whose genome comprises a modified SEQ ID NO: 2 encoding the MSP-1 or fragment thereof operably linked to a mammary gland promoter, wherein the modification reduces the AT content of SEQ ID NO: 2 to 50% or less by replacement of protozoan codons with codons preferred by mammalian cells, wherein the replacement codons each encode the same amino acid as the replaced codon; and allowing the transgenic mammal to express said modified SEQ ID NO: 2, thereby producing MSP-1 in its milk, wherein the MSP-1 or fragment thereof lacks at least one glycosylation site.

7. The composition of claim 6, wherein the MSP-1 or fragment thereof lacks all glycosylation sites.

8. The composition of claim 6, wherein the modified SEQ ID NO: 2 codes for an amino acid substitution at position 182.

9. The composition of claim 6, wherein the modified SEQ ID NO: 2 codes for an amino acid substitution at position 263.

10. The composition of claim 6, wherein the modified SEQ ID NO: 2 codes for amino acid substitutions at positions 182 and 263.

11. The composition of claim 6, wherein the promoter is a β-casein promoter.

12. A composition comprising a merozoite surface protein 1 (MSP-1) or fragment thereof produced by:
providing a non-human transgenic mammal whose genome comprises a modified SEQ ID NO: 2 encoding the MSP-1 or fragment thereof operably linked to a mammary gland promoter, wherein the modification eliminates all the mRNA instability motifs in said SEQ ID NO: 2 by replacement of protozoan codons with codons preferred by mammalian cells, and wherein the replacement codons each encode the same amino acid as the replaced codon; and
allowing the transgenic mammal to express said modified SEQ ID NO: 2, thereby producing MSP-1 in its milk, wherein the MSP-1 or fragment thereof lacks at least one glycosylation site.

13. The composition of claim 12, wherein the MSP-1 or fragment thereof lacks all glycosylation sites.

14. The composition of claim 12, wherein the modified SEQ ID NO: 2 codes for an amino acid substitution at position 182.

15. The composition of claim 12, wherein the modified SEQ ID NO: 2 codes for an amino acid substitution at position 263.

16. The composition of claim 12, wherein the modified SEQ ID NO: 2 codes for amino acid substitutions at positions 182 and 263.

17. The composition of claim 12, wherein the promoter is a β-casein promoter.

18. A composition comprising a merozoite surface protein 1 (MSP-1) or fragment thereof produced by:
providing a non-human transgenic mammal whose genome comprises a modified SEQ ID NO: 2 encoding the MSP-1 or fragment thereof operably linked to a mammary gland promoter, wherein the nucleic acid has been modified by a) elimination of mRNA instability motifs by the replacement of protozoan codons in SEQ ID NO: 2 with codons preferred by mammalian cells and b) reduction of the AT content of SEQ ID NO: 2 to 50% or less by replacement of protozoan codons with codons preferred by mammalian cells, wherein the replacement codons each encode the same amino acid as the replaced codon; and
allowing the transgenic mammal to express said modified SEQ ID NO: 2, thereby producing MSP-1 in its milk, wherein the MSP-1 or fragment thereof lacks at least one glycosylation site.

19. The composition of claim 18, wherein the MSP-1 or fragment thereof lacks all glycosylation sites.

20. The composition of claim 18, wherein the modified SEQ ID NO: 2 codes for an amino acid substitution at position 182.

21. The composition of claim 18, wherein the modified SEQ ID NO: 2 codes for an amino acid substitution at position 263.

22. The composition of claim 18, wherein the modified SEQ ID NO: 2 codes for amino acid substitutions at positions 182 and 263.

23. The composition of claim 18, wherein the modified SEQ ID NO: 2 is expressed in milk at a level which is at least 25% more than the wild-type sequence is expressed under the same conditions.

24. The composition of claim 23, wherein the modified SEQ ID NO: 2 is expressed in milk at a level which is at least 50% more than the wild-type nucleic acid sequence is expressed under the same conditions.

25. The composition of claim 24, wherein the modified SEQ ID NO: 2 is expressed in milk at a level which is at least 100% more than the wild-type nucleic acid sequence is expressed under the same conditions.

26. The composition of claim 18, wherein all protozoan codons are replaced with codons preferred by mammalian cells.

27. The composition of claim 18, wherein the promoter is a β-casein promoter.

* * * * *

SEQUENCE LISTING

<160> NUMBER OF SEQ ID NOS: 19

<210> SEQ ID NO 1
<211> LENGTH: 1065
<212> TYPE: DNA
<213> ORGANISM: Plasmodium falciparum
<220> FEATURE:
<221> NAME/KEY: CDS
<222> LOCATION: (1)...(1065)

<400> SEQUENCE: 1

```
gcc gtc act ccc tcc gtc atc gat aac atc ctg tcc aag atc gag aac      48
Ala Val Thr Pro Ser Val Ile Asp Asn Ile Leu Ser Lys Ile Glu Asn
 1               5                  10                  15 gag tac gag gtg ctg tac ctg aag ccg ctg gca ggg gtc tac cgg agc      96
Glu Tyr Glu Val Leu Tyr Leu Lys Pro Leu Ala Gly Val Tyr Arg Ser
             20                  25                  30 ctg aag aag cag ctg gag aac aac gtg atg acc ttc aac gtg aac gtg     144
Leu Lys Lys Gln Leu Glu Asn Asn Val Met Thr Phe Asn Val Asn Val
         35                  40                  45 aag gat atc ctg aac agc cgg ttc aac aag cgg gag aac ttc aag aac     192
Lys Asp Ile Leu Asn Ser Arg Phe Asn Lys Arg Glu Asn Phe Lys Asn
     50                  55                  60 gtg ctg gag agc gat ctg atc ccc tac aag gat ctg acc agc agc aac     240
Val Leu Glu Ser Asp Leu Ile Pro Tyr Lys Asp Leu Thr Ser Ser Asn
 65                  70                  75                  80 tac gtg gtc aag gat ccc tac aag ttc ctg aac aag gag aag aga gat     288
Tyr Val Val Lys Asp Pro Tyr Lys Phe Leu Asn Lys Glu Lys Arg Asp
                 85                  90                  95 aag ttc ctg agc agt tac aac tac atc aag gat agc att gat acc gat     336
Lys Phe Leu Ser Ser Tyr Asn Tyr Ile Lys Asp Ser Ile Asp Thr Asp
            100                 105                 110 atc aac ttc gcc aac gat gtc ctg gga tac tac aag atc ctg tcc gag     384
Ile Asn Phe Ala Asn Asp Val Leu Gly Tyr Tyr Lys Ile Leu Ser Glu
        115                 120                 125 aag tac aag agc gat ctg gat tca atc aag aag tac atc aac gat aag     432
Lys Tyr Lys Ser Asp Leu Asp Ser Ile Lys Lys Tyr Ile Asn Asp Lys
    130                 135                 140 cag gga gag aac gag aag tac ctg ccc ttc ctg aac aac atc gag acc     480
Gln Gly Glu Asn Glu Lys Tyr Leu Pro Phe Leu Asn Asn Ile Glu Thr
145                 150                 155                 160 ctg tac aag acc gtc aac gat aag att gat ctg ttc gtg atc cac ctg     528
Leu Tyr Lys Thr Val Asn Asp Lys Ile Asp Leu Phe Val Ile His Leu
                165                 170                 175 gag gcc aag gtc ctg aac tac aca tat gag aag agc aac gtg gag gtc     576
Glu Ala Lys Val Leu Asn Tyr Thr Tyr Glu Lys Ser Asn Val Glu Val
            180                 185                 190 aag atc aag gag ctg aat tac ctg aag acc atc cag gat aag ctg gcc     624
Lys Ile Lys Glu Leu Asn Tyr Leu Lys Thr Ile Gln Asp Lys Leu Ala
        195                 200                 205 gat ttc aag aag aac aac aac ttc gtc ggg atc gcc gat ctg agc acc     672
Asp Phe Lys Lys Asn Asn Asn Phe Val Gly Ile Ala Asp Leu Ser Thr
    210                 215                 220 gat tac aac cac aac aac ctg ctg acc aag ttc ctg agc acc ggt atg     720
Asp Tyr Asn His Asn Asn Leu Leu Thr Lys Phe Leu Ser Thr Gly Met
225                 230                 235                 240 gtc ttc gaa aac ctg gcc aag acc gtc ctg agc aac ctg ctg gat ggg     768
Val Phe Glu Asn Leu Ala Lys Thr Val Leu Ser Asn Leu Leu Asp Gly
                245                 250                 255
```

```
aac ctg cag ggg atg ctg aac atc agc cag cac cag tgt gtg aag aag      816
Asn Leu Gln Gly Met Leu Asn Ile Ser Gln His Gln Cys Val Lys Lys
            260                 265                 270 cag tgt ccc cag aac agc ggg tgt ttc aga cac ctg gat gag aga gag      864
Gln Cys Pro Gln Asn Ser Gly Cys Phe Arg His Leu Asp Glu Arg Glu
        275                 280                 285 gag tgt aag tgt ctg ctg aac tac aag cag gaa ggt gat aag tgt gtg      912
Glu Cys Lys Cys Leu Leu Asn Tyr Lys Gln Glu Gly Asp Lys Cys Val
    290                 295                 300 gaa aac ccc aat cct act tgt aac gag aac aat ggt gga tgt gat gcc      960
Glu Asn Pro Asn Pro Thr Cys Asn Glu Asn Asn Gly Gly Cys Asp Ala
305                 310                 315                 320 gat gcc aag tgt acc gag gag gat tca ggg agc aac ggg aag aag atc     1008
Asp Ala Lys Cys Thr Glu Glu Asp Ser Gly Ser Asn Gly Lys Lys Ile
                325                 330                 335 acc tgt gag tgt acc aag cct gat tct tat cca ctg ttc gat ggt atc     1056
Thr Cys Glu Cys Thr Lys Pro Asp Ser Tyr Pro Leu Phe Asp Gly Ile
            340                 345                 350 ttc tgt agt                                                         1065
Phe Cys Ser
        355

<210> SEQ ID NO 2
<211> LENGTH: 1088
<212> TYPE: DNA
<213> ORGANISM: Plasmodium falciparum
<220> FEATURE:
<221> NAME/KEY: CDS
<222> LOCATION: (1)...(1083)

<400> SEQUENCE: 2 gca gta act cct tcc gta att gat aac ata ctt tct aaa att gaa aat       48
Ala Val Thr Pro Ser Val Ile Asp Asn Ile Leu Ser Lys Ile Glu Asn
  1               5                  10                  15 gaa tat gag gtt tta tat tta aaa cct tta gca ggt gtt tat aga agt       96
Glu Tyr Glu Val Leu Tyr Leu Lys Pro Leu Ala Gly Val Tyr Arg Ser
             20                  25                  30 tta aaa aaa caa tta gaa aat aac gtt atg aca ttt aat gtt aat gtt      144
Leu Lys Lys Gln Leu Glu Asn Asn Val Met Thr Phe Asn Val Asn Val
         35                  40                  45 aag gat att tta aat tca cga ttt aat aaa cgt gaa aat ttc aaa aat      192
Lys Asp Ile Leu Asn Ser Arg Phe Asn Lys Arg Glu Asn Phe Lys Asn
     50                  55                  60 gtt tta gaa tca gat tta att cca tat aaa gat tta aca tca agt aat      240
Val Leu Glu Ser Asp Leu Ile Pro Tyr Lys Asp Leu Thr Ser Ser Asn
 65                  70                  75                  80 tat gtt gtc aaa gat cca tat aaa ttt ctt aat aaa gaa aaa aga gat      288
Tyr Val Val Lys Asp Pro Tyr Lys Phe Leu Asn Lys Glu Lys Arg Asp
                 85                  90                  95 aaa ttc tta agc agt tat aat tat att aag gat tca ata gat acg gat      336
Lys Phe Leu Ser Ser Tyr Asn Tyr Ile Lys Asp Ser Ile Asp Thr Asp
            100                 105                 110 ata aat ttt gca aat gat gtt ctt gga tat tat aaa ata tta tcc gaa      384
Ile Asn Phe Ala Asn Asp Val Leu Gly Tyr Tyr Lys Ile Leu Ser Glu
        115                 120                 125 aaa tat aaa tca gat tta gat tca att aaa aaa tat atc aac gac aaa      432
Lys Tyr Lys Ser Asp Leu Asp Ser Ile Lys Lys Tyr Ile Asn Asp Lys
    130                 135                 140 caa ggt gaa aat gag aaa tac ctt ccc ttt tta aac aat att gag acc      480
Gln Gly Glu Asn Glu Lys Tyr Leu Pro Phe Leu Asn Asn Ile Glu Thr
145                 150                 155                 160
```

-continued

| | |
|---|---|
| tta tat aaa aca gtt aat gat aaa att gat tta ttt gta att cat tta<br>Leu Tyr Lys Thr Val Asn Asp Lys Ile Asp Leu Phe Val Ile His Leu<br>              165                    170                    175 | 528 |
| gaa gca aaa gtt cta aat tat aca tat gag aaa tca aac gta gaa gtt<br>Glu Ala Lys Val Leu Asn Tyr Thr Tyr Glu Lys Ser Asn Val Glu Val<br>        180                        185                        190 | 576 |
| aaa ata aaa gaa ctt aat tac tta aaa aca att caa gac aaa ttg gca<br>Lys Ile Lys Glu Leu Asn Tyr Leu Lys Thr Ile Gln Asp Lys Leu Ala<br>            195                      200                    205 | 624 |
| gat ttt aaa aaa aat aac aat ttc gtt gga att gct gat tta tca aca<br>Asp Phe Lys Lys Asn Asn Asn Phe Val Gly Ile Ala Asp Leu Ser Thr<br>210                    215                    220 | 672 |
| gat tat aac cat aat aac tta ttg aca aag ttc ctt agt aca ggt atg<br>Asp Tyr Asn His Asn Asn Leu Leu Thr Lys Phe Leu Ser Thr Gly Met<br>225                    230                    235                    240 | 720 |
| gtt ttt gaa aat ctt gct aaa acc gtt tta tct aat tta ctt gat gga<br>Val Phe Glu Asn Leu Ala Lys Thr Val Leu Ser Asn Leu Leu Asp Gly<br>                245                    250                    255 | 768 |
| aac ttg caa ggt atg tta aac att tca caa cac caa tgc gta aaa aaa<br>Asn Leu Gln Gly Met Leu Asn Ile Ser Gln His Gln Cys Val Lys Lys<br>        260                        265                        270 | 816 |
| caa tgt cca caa aat tct gga tgt ttc aga cat tta gat gaa aga gaa<br>Gln Cys Pro Gln Asn Ser Gly Cys Phe Arg His Leu Asp Glu Arg Glu<br>            275                      280                    285 | 864 |
| gaa tgt aaa tgt tta tta aat tac aaa caa gaa ggt gat aaa tgt gtt<br>Glu Cys Lys Cys Leu Leu Asn Tyr Lys Gln Glu Gly Asp Lys Cys Val<br>        290                        295                    300 | 912 |
| gaa aat cca aat cct act tgt aac gaa aat aat ggt gga tgt gat gca<br>Glu Asn Pro Asn Pro Thr Cys Asn Glu Asn Asn Gly Gly Cys Asp Ala<br>305                    310                    315                    320 | 960 |
| gat gcc aaa tgt acc gaa gaa gat tca ggt agc aac gga aag aaa atc<br>Asp Ala Lys Cys Thr Glu Glu Asp Ser Gly Ser Asn Gly Lys Lys Ile<br>            325                      330                    335 | 1008 |
| aca tgt gaa tgt act aaa cct gat tct tat cca ctt ttc gat ggt att<br>Thr Cys Glu Cys Thr Lys Pro Asp Ser Tyr Pro Leu Phe Asp Gly Ile<br>        340                        345                    350 | 1056 |
| ttc tgc agt cac cac cac cac cac cac taact<br>Phe Cys Ser His His His His His His<br>            355                      360 | 1088 |

```
<210> SEQ ID NO 3
<211> LENGTH: 88
<212> TYPE: DNA
<213> ORGANISM: Plasmodium falciparum

<400> SEQUENCE: 3
tcgacgagag ccatgaaggt cctcatcctt gcctgtctgg tggctctggc cattgcaaga      60
gagcaggaag aactcaatgt agtcggta                                        88

<210> SEQ ID NO 4
<211> LENGTH: 88
<212> TYPE: DNA
<213> ORGANISM: Plasmodium falciparum

<400> SEQUENCE: 4
gatctaccga ctacattgag ttcttcctgc tctcttgcaa tggccagagc caccagacag      60
gcaaggatga ggaccttcat ggctctcg                                        88

<210> SEQ ID NO 5
<211> LENGTH: 60
```

```
<212> TYPE: DNA
<213> ORGANISM: Plasmodium falciparum

<400> SEQUENCE: 5
taactcgagc gaaccatgaa ggtcctcatc cttgcctgtc tggtggctct ggccattgca      60

<210> SEQ ID NO 6
<211> LENGTH: 48
<212> TYPE: DNA
<213> ORGANISM: Plasmodium falciparum

<400> SEQUENCE: 6
aattctcgag ttagtggtgg tggtggtggt gactgcagaa ataccatc                   48

<210> SEQ ID NO 7
<211> LENGTH: 31
<212> TYPE: DNA
<213> ORGANISM: Plasmodium falciparum

<400> SEQUENCE: 7
aatagatctg cagtaactcc ttccgtaatt g                                     31

<210> SEQ ID NO 8
<211> LENGTH: 1142
<212> TYPE: DNA
<213> ORGANISM: Plasmodium falciparum
<220> FEATURE:
<221> NAME/KEY: CDS
<222> LOCATION: (1)...(1142)

<400> SEQUENCE: 8
```

| | | | | | | | | | | | | | | | | |
|---|---|---|---|---|---|---|---|---|---|---|---|---|---|---|---|---|
| atg | aag | gtc | ctc | ata | att | gcc | tgt | ctg | gtg | gct | ctg | gcc | att | gca | gcc | 48 |
| Met | Lys | Val | Leu | Ile | Ile | Ala | Cys | Leu | Val | Ala | Leu | Ala | Ile | Ala | Ala | |
| 1 | | | | 5 | | | | | 10 | | | | | 15 | | |
| gtc | act | ccc | tcc | gtc | atc | gat | aac | atc | ctg | tcc | aag | atc | gag | aac | gag | 96 |
| Val | Thr | Pro | Ser | Val | Ile | Asp | Asn | Ile | Leu | Ser | Lys | Ile | Glu | Asn | Glu | |
| | | | 20 | | | | | 25 | | | | | 30 | | | |
| tac | gag | gtg | ctg | tac | ctg | aag | ccc | ctg | gca | gga | gtc | tac | agg | agc | ctg | 144 |
| Tyr | Glu | Val | Leu | Tyr | Leu | Lys | Pro | Leu | Ala | Gly | Val | Tyr | Arg | Ser | Leu | |
| | | 35 | | | | | 40 | | | | | 45 | | | | |
| aag | aag | cag | ctg | gag | aac | aac | gtg | atg | acc | ttc | aac | gtg | aac | gtg | aag | 192 |
| Lys | Lys | Gln | Leu | Glu | Asn | Asn | Val | Met | Thr | Phe | Asn | Val | Asn | Val | Lys | |
| | 50 | | | | | 55 | | | | | 60 | | | | | |
| gat | atc | ctg | aac | agc | agg | ttc | aac | aag | agg | gag | aac | ttc | aag | aac | gtg | 240 |
| Asp | Ile | Leu | Asn | Ser | Arg | Phe | Asn | Lys | Arg | Glu | Asn | Phe | Lys | Asn | Val | |
| 65 | | | | | 70 | | | | | 75 | | | | | 80 | |
| ctg | gag | agc | gat | ctg | atc | ccc | tac | aag | gat | ctg | acc | agc | agc | aac | tac | 288 |
| Leu | Glu | Ser | Asp | Leu | Ile | Pro | Tyr | Lys | Asp | Leu | Thr | Ser | Ser | Asn | Tyr | |
| | | | | 85 | | | | | 90 | | | | | 95 | | |
| gtg | gtc | aaa | gat | ccc | tac | aag | ttc | ctg | aac | aag | gag | aag | aga | gat | aag | 336 |
| Val | Val | Lys | Asp | Pro | Tyr | Lys | Phe | Leu | Asn | Lys | Glu | Lys | Arg | Asp | Lys | |
| | | | 100 | | | | | 105 | | | | | 110 | | | |
| ttc | ctg | agc | agt | tac | aat | tac | atc | aag | gat | agc | att | gac | acc | gat | atc | 384 |
| Phe | Leu | Ser | Ser | Tyr | Asn | Tyr | Ile | Lys | Asp | Ser | Ile | Asp | Thr | Asp | Ile | |
| | | 115 | | | | | 120 | | | | | 125 | | | | |
| aac | ttc | gcc | aac | gat | gtc | ctg | gga | tac | tac | aag | atc | ctg | tcc | gag | aag | 432 |
| Asn | Phe | Ala | Asn | Asp | Val | Leu | Gly | Tyr | Tyr | Lys | Ile | Leu | Ser | Glu | Lys | |
| | 130 | | | | | 135 | | | | | 140 | | | | | |
| tac | aag | agc | gat | ctg | gat | agc | atc | aag | aag | tac | atc | aac | gat | aag | cag | 480 |
| Tyr | Lys | Ser | Asp | Leu | Asp | Ser | Ile | Lys | Lys | Tyr | Ile | Asn | Asp | Lys | Gln | |
| 145 | | | | | 150 | | | | | 155 | | | | | 160 | |
| gga | gag | aac | gag | aag | tac | ctg | ccc | ttc | ctg | aac | aac | atc | gag | acc | ctg | 528 |

```
                Gly Glu Asn Glu Lys Tyr Leu Pro Phe Leu Asn Asn Ile Glu Thr Leu
                            165                 170                 175 tac aag acc gtc aac gat aag att gat ctg ttc gtg atc cac ctg gag                 576
Tyr Lys Thr Val Asn Asp Lys Ile Asp Leu Phe Val Ile His Leu Glu
            180                 185                 190 gcc aag gtc ctg cag tac aca tat gag aag agc aac gtg gag gtc aag                 624
Ala Lys Val Leu Gln Tyr Thr Tyr Glu Lys Ser Asn Val Glu Val Lys
        195                 200                 205 atc aag gag ctg aat tac ctg aag acc atc cag gat aag ctg gcc gat                 672
Ile Lys Glu Leu Asn Tyr Leu Lys Thr Ile Gln Asp Lys Leu Ala Asp
    210                 215                 220 ttc aag aag aac aac aac ttc gtc gga atc gcc gat ctg agc acc gat                 720
Phe Lys Lys Asn Asn Asn Phe Val Gly Ile Ala Asp Leu Ser Thr Asp
225                 230                 235                 240 tac aac cac aac aac ctg ctg acc aag ttc ctg agc acc gga atg gtc                 768
Tyr Asn His Asn Asn Leu Leu Thr Lys Phe Leu Ser Thr Gly Met Val
                245                 250                 255 ttc gaa aac ctg gcc aag acc gtc ctg agc aac ctg ctg gat gga aac                 816
Phe Glu Asn Leu Ala Lys Thr Val Leu Ser Asn Leu Leu Asp Gly Asn
            260                 265                 270 ctg cag gga atg ctg cag atc agc cag cac cag tgt gtg aag aag cag                 864
Leu Gln Gly Met Leu Gln Ile Ser Gln His Gln Cys Val Lys Lys Gln
        275                 280                 285 tgt ccc cag aac agc gga tgc ttc aga cac ctg gat gag agg gag gag                 912
Cys Pro Gln Asn Ser Gly Cys Phe Arg His Leu Asp Glu Arg Glu Glu
    290                 295                 300 tgc aag tgc ctg ctg aac tac aag cag gaa gga gat aag tgt gtg gaa                 960
Cys Lys Cys Leu Leu Asn Tyr Lys Gln Glu Gly Asp Lys Cys Val Glu
305                 310                 315                 320 aac ccc aat cct act tgt aac gag aac aat gga gga tgc gat gcc gat                1008
Asn Pro Asn Pro Thr Cys Asn Glu Asn Asn Gly Gly Cys Asp Ala Asp
                325                 330                 335 gcc aag tgt acc gag gag gat tca gga agc aac gga aag aag atc acc                1056
Ala Lys Cys Thr Glu Glu Asp Ser Gly Ser Asn Gly Lys Lys Ile Thr
            340                 345                 350 tgc gag tgt acc aag cct gat tct tat cca ctg ttc gat ggt att ttc                1104
Cys Glu Cys Thr Lys Pro Asp Ser Tyr Pro Leu Phe Asp Gly Ile Phe
        355                 360                 365 tgc agt cac cac cac cac cac cac taa ctc gag gat cc                             1142
Cys Ser His His His His His His  *  Leu Glu Asp
    370                 375

<210> SEQ ID NO 9
<211> LENGTH: 355
<212> TYPE: PRT
<213> ORGANISM: Plasmodium falciparum

<400> SEQUENCE: 9

Ala Val Thr Pro Ser Val Ile Asp Asn Ile Leu Ser Lys Ile Glu Asn
1               5                   10                  15

Glu Tyr Glu Val Leu Tyr Leu Lys Pro Leu Ala Gly Val Tyr Arg Ser
            20                  25                  30

Leu Lys Lys Gln Leu Glu Asn Val Met Thr Phe Asn Val Asn Val
        35                  40                  45

Lys Asp Ile Leu Asn Ser Arg Phe Asn Lys Arg Glu Asn Phe Lys Asn
    50                  55                  60

Val Leu Glu Ser Asp Leu Ile Pro Tyr Lys Asp Leu Thr Ser Ser Asn
65                  70                  75                  80

Tyr Val Val Lys Asp Pro Tyr Lys Phe Leu Asn Lys Glu Lys Arg Asp
```

```
                            85                  90                  95
Lys Phe Leu Ser Ser Tyr Asn Tyr Ile Lys Asp Ser Ile Asp Thr Asp
            100                 105                 110

Ile Asn Phe Ala Asn Asp Val Leu Gly Tyr Tyr Lys Ile Leu Ser Glu
            115                 120                 125

Lys Tyr Lys Ser Asp Leu Asp Ser Ile Lys Lys Tyr Ile Asn Asp Lys
            130                 135                 140

Gln Gly Glu Asn Glu Lys Tyr Leu Pro Phe Leu Asn Asn Ile Glu Thr
145                 150                 155                 160

Leu Tyr Lys Thr Val Asn Asp Lys Ile Asp Leu Phe Val Ile His Leu
                165                 170                 175

Glu Ala Lys Val Leu Asn Tyr Thr Tyr Glu Lys Ser Asn Val Glu Val
            180                 185                 190

Lys Ile Lys Glu Leu Asn Tyr Leu Lys Thr Ile Gln Asp Lys Leu Ala
            195                 200                 205

Asp Phe Lys Lys Asn Asn Phe Val Gly Ile Ala Asp Leu Ser Thr
            210                 215                 220

Asp Tyr Asn His Asn Asn Leu Leu Thr Lys Phe Leu Ser Thr Gly Met
225                 230                 235                 240

Val Phe Glu Asn Leu Ala Lys Thr Val Leu Ser Asn Leu Leu Asp Gly
            245                 250                 255

Asn Leu Gln Gly Met Leu Asn Ile Ser Gln His Gln Cys Val Lys Lys
            260                 265                 270

Gln Cys Pro Gln Asn Ser Gly Cys Phe Arg His Leu Asp Glu Arg Glu
            275                 280                 285

Glu Cys Lys Cys Leu Leu Asn Tyr Lys Gln Glu Gly Asp Lys Cys Val
            290                 295                 300

Glu Asn Pro Asn Pro Thr Cys Asn Glu Asn Asn Gly Gly Cys Asp Ala
305                 310                 315                 320

Asp Ala Lys Cys Thr Glu Glu Asp Ser Gly Ser Asn Gly Lys Lys Ile
                325                 330                 335

Thr Cys Glu Cys Thr Lys Pro Asp Ser Tyr Pro Leu Phe Asp Gly Ile
            340                 345                 350

Phe Cys Ser
        355

<210> SEQ ID NO 10
<211> LENGTH: 361
<212> TYPE: PRT
<213> ORGANISM: Plasmodium falciparum

<400> SEQUENCE: 10

Ala Val Thr Pro Ser Val Ile Asp Asn Ile Leu Ser Lys Ile Glu Asn
1               5                   10                  15

Glu Tyr Glu Val Leu Tyr Leu Lys Pro Leu Ala Gly Val Tyr Arg Ser
                20                  25                  30

Leu Lys Lys Gln Leu Glu Asn Asn Val Met Thr Phe Asn Val Asn Val
            35                  40                  45

Lys Asp Ile Leu Asn Ser Arg Phe Asn Lys Arg Glu Asn Phe Lys Asn
        50                  55                  60

Val Leu Glu Ser Asp Leu Ile Pro Tyr Lys Asp Leu Thr Ser Ser Asn
65                  70                  75                  80

Tyr Val Val Lys Asp Pro Tyr Lys Phe Leu Asn Lys Glu Lys Arg Asp
                85                  90                  95
```

-continued

```
Lys Phe Leu Ser Ser Tyr Asn Tyr Ile Lys Asp Ser Ile Asp Thr Asp
                100                 105                 110

Ile Asn Phe Ala Asn Asp Val Leu Gly Tyr Tyr Lys Ile Leu Ser Glu
            115                 120                 125

Lys Tyr Lys Ser Asp Leu Asp Ser Ile Lys Lys Tyr Ile Asn Asp Lys
        130                 135                 140

Gln Gly Glu Asn Glu Lys Tyr Leu Pro Phe Leu Asn Asn Ile Glu Thr
145                 150                 155                 160

Leu Tyr Lys Thr Val Asn Asp Lys Ile Asp Leu Phe Val Ile His Leu
                165                 170                 175

Glu Ala Lys Val Leu Asn Tyr Thr Tyr Glu Lys Ser Asn Val Glu Val
            180                 185                 190

Lys Ile Lys Glu Leu Asn Tyr Leu Lys Thr Ile Gln Asp Lys Leu Ala
        195                 200                 205

Asp Phe Lys Lys Asn Asn Phe Val Gly Ile Ala Asp Leu Ser Thr
            210                 215                 220

Asp Tyr Asn His Asn Asn Leu Leu Thr Lys Phe Leu Ser Thr Gly Met
225                 230                 235                 240

Val Phe Glu Asn Leu Ala Lys Thr Val Leu Ser Asn Leu Leu Asp Gly
                245                 250                 255

Asn Leu Gln Gly Met Leu Asn Ile Ser Gln His Gln Cys Val Lys Lys
            260                 265                 270

Gln Cys Pro Gln Asn Ser Gly Cys Phe Arg His Leu Asp Glu Arg Glu
        275                 280                 285

Glu Cys Lys Cys Leu Leu Asn Tyr Lys Gln Glu Gly Asp Lys Cys Val
    290                 295                 300

Glu Asn Pro Asn Pro Thr Cys Asn Glu Asn Asn Gly Gly Cys Asp Ala
305                 310                 315                 320

Asp Ala Lys Cys Thr Glu Glu Asp Ser Gly Ser Asn Gly Lys Lys Ile
                325                 330                 335

Thr Cys Glu Cys Thr Lys Pro Asp Ser Tyr Pro Leu Phe Asp Gly Ile
            340                 345                 350

Phe Cys Ser His His His His His His
        355                 360

<210> SEQ ID NO 11
<211> LENGTH: 379
<212> TYPE: PRT
<213> ORGANISM: Plasmodium falciparum

<400> SEQUENCE: 11

Met Lys Val Leu Ile Ile Ala Cys Leu Val Ala Leu Ala Ile Ala Ala
1               5                   10                  15

Val Thr Pro Ser Val Ile Asp Asn Ile Leu Ser Lys Ile Glu Asn Glu
            20                  25                  30

Tyr Glu Val Leu Tyr Leu Lys Pro Leu Ala Gly Val Tyr Arg Ser Leu
        35                  40                  45

Lys Lys Gln Leu Glu Asn Asn Val Met Thr Phe Asn Val Asn Val Lys
    50                  55                  60

Asp Ile Leu Asn Ser Arg Phe Asn Lys Arg Glu Asn Phe Lys Asn Val
65                  70                  75                  80

Leu Glu Ser Asp Leu Ile Pro Tyr Lys Asp Leu Thr Ser Ser Asn Tyr
                85                  90                  95

Val Val Lys Asp Pro Tyr Lys Phe Leu Asn Lys Glu Lys Arg Asp Lys
            100                 105                 110
```

Phe Leu Ser Ser Tyr Asn Tyr Ile Lys Asp Ser Ile Asp Thr Asp Ile
            115                 120                 125

Asn Phe Ala Asn Asp Val Leu Gly Tyr Tyr Lys Ile Leu Ser Glu Lys
        130                 135                 140

Tyr Lys Ser Asp Leu Asp Ser Ile Lys Lys Tyr Ile Asn Asp Lys Gln
145                 150                 155                 160

Gly Glu Asn Glu Lys Tyr Leu Pro Phe Leu Asn Asn Ile Glu Thr Leu
                165                 170                 175

Tyr Lys Thr Val Asn Asp Lys Ile Asp Leu Phe Val Ile His Leu Glu
            180                 185                 190

Ala Lys Val Leu Gln Tyr Thr Tyr Glu Lys Ser Asn Val Glu Val Lys
        195                 200                 205

Ile Lys Glu Leu Asn Tyr Leu Lys Thr Ile Gln Asp Lys Leu Ala Asp
        210                 215                 220

Phe Lys Lys Asn Asn Phe Val Gly Ile Ala Asp Leu Ser Thr Asp
225                 230                 235                 240

Tyr Asn His Asn Asn Leu Leu Thr Lys Phe Leu Ser Thr Gly Met Val
                245                 250                 255

Phe Glu Asn Leu Ala Lys Thr Val Leu Ser Asn Leu Leu Asp Gly Asn
            260                 265                 270

Leu Gln Gly Met Leu Gln Ile Ser Gln His Gln Cys Val Lys Lys Gln
        275                 280                 285

Cys Pro Gln Asn Ser Gly Cys Phe Arg His Leu Asp Glu Arg Glu Glu
        290                 295                 300

Cys Lys Cys Leu Leu Asn Tyr Lys Gln Glu Gly Asp Lys Cys Val Glu
305                 310                 315                 320

Asn Pro Asn Pro Thr Cys Asn Glu Asn Asn Gly Gly Cys Asp Ala Asp
                325                 330                 335

Ala Lys Cys Thr Glu Glu Asp Ser Gly Ser Asn Gly Lys Lys Ile Thr
            340                 345                 350

Cys Glu Cys Thr Lys Pro Asp Ser Tyr Pro Leu Phe Asp Gly Ile Phe
        355                 360                 365

Cys Ser His His His His His His Leu Glu Asp
        370                 375

<210> SEQ ID NO 12
<211> LENGTH: 82
<212> TYPE: DNA
<213> ORGANISM: Artificial Sequence
<220> FEATURE:
<223> OTHER INFORMATION: Synthetically generated primer

<400> SEQUENCE: 12
ggccgctcga cgccaccatg aaggtcctca taattgcctg tctggtggct ctggccattg    60
cagccgtcac tccctccgtc at                                              82

<210> SEQ ID NO 13
<211> LENGTH: 80
<212> TYPE: DNA
<213> ORGANISM: Artificial Sequence
<220> FEATURE:
<223> OTHER INFORMATION: Synthetically generated primer

<400> SEQUENCE: 13
cgatgacgga gggagtgacg gctgcaatgg ccagagccac cagacaggca attatgagga    60
ccttcatggt ggcgtcgagc                                                 80

<210> SEQ ID NO 14
<211> LENGTH: 27
<212> TYPE: DNA
<213> ORGANISM: Artificial Sequence
<220> FEATURE:
<223> OTHER INFORMATION: Synthetically generated primer

<400> SEQUENCE: 14
gattgacaag taatacgctg tttcctc                                    27

<210> SEQ ID NO 15
<211> LENGTH: 17
<212> TYPE: DNA
<213> ORGANISM: Artificial Sequence
<220> FEATURE:
<223> OTHER INFORMATION: Synthetically generated primer

<400> SEQUENCE: 15
ggattcaata gatacgg                                               17

<210> SEQ ID NO 16
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 16
cagggaatgc tgcagatcag c                                          21

<210> SEQ ID NO 17
<211> LENGTH: 49
<212> TYPE: DNA
<213> ORGANISM: Artificial Sequence
<220> FEATURE:
<223> OTHER INFORMATION: Synthetically generated primer

<400> SEQUENCE: 17
aattctcgag ttagtggtgg tggtggtggt gatcgcagaa aataccatg            49

<210> SEQ ID NO 18
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 18
ctccttgttc aggaacttgt aggg                                       24

<210> SEQ ID NO 19
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 19
gtcctgcagt acacatatga g                                          21